US006491965B1

(12) United States Patent
Berry et al.

(10) Patent No.: US 6,491,965 B1
(45) Date of Patent: Dec. 10, 2002

(54) MEDICAL DEVICE COMPRISING GLYCOSAMINOGLYCAN-ANTITHROMBIN III/HEPARIN COFACTOR II CONJUGATES

(75) Inventors: Leslie Berry, Burlington (CA); Maureen Andrew, Oakville (CA)

(73) Assignee: Hamilton Civic Hospitals Research Development, Inc., Hamilton (CA)

( * ) Notice: Subject to any disclaimer, the term of this patent is extended or adjusted under 35 U.S.C. 154(b) by 0 days.

(21) Appl. No.: 08/768,035

(22) Filed: Dec. 17, 1996

Related U.S. Application Data

(63) Continuation-in-part of application No. 08/564,976, filed on Nov. 30, 1995.

(30) Foreign Application Priority Data

May 8, 1998 (CA) .............................................. 2237159

(51) Int. Cl.⁷ ....................... A61L 27/00; C07K 14/435; A61K 38/16; A61K 6/00

(52) U.S. Cl. ...................... 427/2.1; 427/2.24; 427/2.29; 514/2; 530/350; 530/393; 536/21

(58) Field of Search ................................. 530/300, 350, 530/393; 536/21; 260/123.7; 514/2, 21; 427/2.24, 2.29, 2.1

(56) References Cited

U.S. PATENT DOCUMENTS

| | | | |
|---|---|---|---|
| 2,824,092 A | 2/1958 | Thompson | |
| 3,616,935 A | 11/1971 | Love et al. | |
| 3,673,612 A | 7/1972 | Merrill et al. | |
| 3,842,061 A | 10/1974 | Andersson et al. | |
| 4,055,635 A | 10/1977 | Green et al. | |
| 4,213,962 A | 7/1980 | Miura et al. | |
| 4,301,153 A | 11/1981 | Rosenberg | |
| 4,340,589 A | 7/1982 | Uemura et al. | |
| 4,356,170 A | 10/1982 | Jennings et al. | |
| 4,446,126 A | 5/1984 | Jordan | |
| 4,448,718 A * | 5/1984 | Yannas et al. | 260/123.7 |
| 4,465,623 A | 8/1984 | Chanas et al. | |
| 4,496,550 A | 1/1985 | Lindahl et al. | |
| 4,510,084 A | 4/1985 | Eibl et al. | |
| 4,526,714 A | 7/1985 | Feijen et al. | |
| 4,585,754 A | 4/1986 | Meisner et al. | |
| 4,613,665 A | 9/1986 | Larm | |
| 4,623,718 A | 11/1986 | Collen | 530/393 |
| 4,634,762 A * | 1/1987 | Feijen et al. | 530/350 |
| 4,656,161 A | 4/1987 | Herr | |
| 4,678,671 A * | 7/1987 | Feijen et al. | 424/443 |
| 4,689,323 A | 8/1987 | Mitra et al. | 514/56 |
| 4,731,073 A | 3/1988 | Robinson | |
| 4,863,907 A | 9/1989 | Sakurai et al. | |
| 4,920,194 A | 4/1990 | Feller et al. | |
| 4,935,204 A | 6/1990 | Seidel et al. | |
| 4,987,181 A | 1/1991 | Bichon et al. | |
| 4,990,502 A | 2/1991 | Lormeau et al. | 514/56 |
| 5,002,582 A | 3/1991 | Guire et al. | |
| 5,023,078 A * | 6/1991 | Halluin | 424/94.64 |
| 5,061,750 A | 10/1991 | Feijen et al. | |
| 5,071,973 A | 12/1991 | Keller et al. | |
| 5,084,273 A | 1/1992 | Hirahara | |
| 5,134,192 A | 7/1992 | Feijen et al. | |
| 5,159,050 A | 10/1992 | Onwumere | |
| 5,171,264 A | 12/1992 | Merrill | |
| 5,182,259 A | 1/1993 | Kita | |
| 5,182,317 A | 1/1993 | Winters et al. | |
| 5,222,971 A | 6/1993 | Willard et al. | |
| 5,262,451 A | 11/1993 | Winters et al. | |
| 5,270,046 A | 12/1993 | Sakamoto et al. | |
| 5,275,838 A | 1/1994 | Merrill | |
| 5,280,016 A | 1/1994 | Conrad et al. | 514/56 |
| 5,308,617 A | 5/1994 | Halluin | 424/54.64 |
| 5,310,881 A | 5/1994 | Sakurai et al. | |
| 5,319,072 A | 6/1994 | Uemura et al. | |
| 5,330,907 A | 7/1994 | Philapitsch et al. | |
| 5,338,770 A | 8/1994 | Winters et al. | |
| 5,364,350 A | 11/1994 | Dittmann | |
| 5,436,291 A | 7/1995 | Levy et al. | |
| 5,455,040 A | 10/1995 | Marchant | |
| 5,510,418 A | 4/1996 | Rhee et al. | 525/54.2 |
| 5,529,986 A | 6/1996 | Larsson et al. | |
| 5,589,516 A | 12/1996 | Uriyu et al. | |
| 5,652,014 A | 7/1997 | Galin et al. | |
| 5,741,852 A | 4/1998 | Marchant et al. | |
| 5,741,881 A | 4/1998 | Patnaik | |
| 5,762,944 A | 6/1998 | Inoue et al. | |
| 5,782,908 A | 7/1998 | Cahalan et al. | |

(List continued on next page.)

FOREIGN PATENT DOCUMENTS

| | | |
|---|---|---|
| EP | 0 081 853 | 6/1983 |
| EP | 0 098 814 | 1/1984 |
| EP | 0 137 356 | 4/1985 |
| EP | 0 344 068 | 11/1989 |
| EP | 0 345 616 | 12/1989 |
| FR | 2 635 019 | 2/1990 |
| WO | 89/09624 | 10/1989 |
| WO | 90/01332 | 2/1990 |

OTHER PUBLICATIONS

Berry et al. (1998) J. Biochem. 124:434–439.*
Radoff, et al., *Radioreceptor Assay for Advanced Glycosylation End Products*, Diabetes, vol. 40, pp. 1731–1738, Dec. 1991.

(List continued on next page.)

*Primary Examiner*—Michael Pak
(74) *Attorney, Agent, or Firm*—Millen, White, Zelano & Branigan, P.C.

(57) ABSTRACT

Novel conjugates of glycosaminoglycans, particularly heparin and dermatan sulfate, and amine containing species and therapeutic uses thereof are described. In particular, mild methods of conjugating heparins to proteins, such as antithrombin III and heparin cofactor II, which provide covalent conjugates which retain maximal biological activity are described. Uses of these conjugates to prevent thrombogenesis, in particular in lung airways, such as found in infant and adult respiratory distress syndrome, and on surfaces in contact with blood are also described.

59 Claims, 28 Drawing Sheets

U.S. PATENT DOCUMENTS

| | | | |
|---|---|---|---|
| 5,843,172 | A | 12/1998 | Yan |
| 5,851,229 | A | 12/1998 | Lentz et al. |
| 5,855,618 | A | 1/1999 | Patnaik et al. |
| 5,866,113 | A | 2/1999 | Hendriks et al. |
| 5,876,433 | A | 3/1999 | Lunn |
| 5,879,697 | A | 3/1999 | Ding et al. |
| 5,891,196 | A | 4/1999 | Lee et al. |
| 5,944,753 | A | 8/1999 | Galin et al. |
| 5,945,457 | A | 8/1999 | Plate et al. |
| 5,955,438 | A | 9/1999 | Pitaru et al. |
| 6,024,918 | A | 2/2000 | Hendriks et al. |
| 2001/0007063 | A1 | 7/2001 | Oyama et al. |
| 2001/0034336 | A1 | 10/2001 | Shah et al. |

OTHER PUBLICATIONS

Takuya Fujuita et al., "Alteration of biopharmaceutical properties of drugs by their conjugation with water–soluble macromolecules: uricase–dextran conjugate," *Journal of Controlled Release*, vol. 11, pp. 149–156 (1990).

Te Piao King et al., "Immunochemical studies of dextran coupled ragweed pollen allergen, antigen E$^1$," *Archives of Biochemistry and Biophysics*, pp. 464–473 (1975).

Fu–Tong Liu et al., "Immunological tolerance to allergenic protein determinants: A therapeutic approach for selective inhibition of IgE antibody production," *Proc. Natl. Acad. Sci. USA*, vol. 76, No. 3, pp. 1430–1434 (1979).

Hiroshi Maeda et al., "Conjugation of Poly(stryrene–co–maleic acid) derivatives to the antitumor protein neocarzinostatin: pronounced improvements in pharmacological properties," *J. Med. Chem.*, vol. 28, pp. 455–461 (1985).

M. Okada et al., "Suppression of IgE antibody response against ovalbumin by the chemical conjugate of ovalbumin with a polyaspartic acid derivative," *Int. Archs Allergy appl. Immun.*, vol. 76, pp. 79–81 (1985).

Mitsuko Usui et al., "IgE–selecive and antigen–specific unresponsiveness in mice," *The Journal of Immunology*, vol. 122, No. 4, pp. 1266–1272 (1979).

I. Bjork et al., "Permanent Activation of Antithrombin by Covalent Attachment of Heparin Oligosaccharides," *FEBS Letters*, vol. No. 143, 1982, pp. 96–100.

R. Ceustermans et al., "Preparation, Characterization, and Turnover Properties of Heparin–Antithrombin III Complexes Stabilized by Covalent Bonds," *The Journal of Biological Chemistry*, vol. 257, 1982, pp. 3401–3408.

M.W.C. Hatton et al., "Tritiation of Commercial Heparins by Reaction with NaB$^3$H$_4$: Chemical Analysis and Biological Properties of the Product," *Analytical Biochemistry*, vol. 106, 1980, pp. 417–426.

M. Hoylaerts et al., "Covalent Complexes Between Low Molecular Weight Heparin Fragments and Antithrombin III–Inhibition Kinetics and Turnover Parameters," *Thromb Haemostas*, vol. 49, 1983, pp. 109–115.

M. Hoylaerts et al., "Involvement of Heparin Chain Length in the Heparin–catalyzed Inhibition of Thrombin by Antithrombin III," *The Journal of Biological Chemistry*, vol. 259, 1984, pp. 5670–5677.

C. Mattson et al., "Antithrombic Properties in Rabbits of Heparin and Heparin Fragments Covalently Coupled to Human Antithrombin III," *J. Clin. Invest.*, vol. 75, 1985, pp. 1169–1173.

Maimone, M.M., et al., "Structure of a Dermatan Sulfate Hexasaccharide That Binds to Heparin Cofactor II With High Affinity," *J. of Bio. Chem.*, vol. 265, No. 30, pp. 18263–18271 (1990).

Uno, Takeji, et al., "Evaluation for antithrombogenicity on the surface of heparinized biomedical material using thrombin–antithrombin III complex," *Chemical Abstracts*, vol. 122, No. 25, Abstract No. 306176 (Jun. 19, 1995).

Hatton, M.W.C., et al., "Inhibition of Thrombin by Antithrombin III in the Presence of Certain Glycosaminoglycans Found in the Mammalian Aorta," *Thrombosis Research*, 13:4, 655–670 (Apr. 24, 1978).

Verstraete, M., "Prevention of Thrombosis in Arteries: Novel Approaches," *J. Cardiovasc. Pharmacol.*, 7(Suppl. 3) S191–S205 (1985).

* cited by examiner

* bleeding less than 200 microlitre considered acceptable

Luminal Surface of Tubing After Exposed to Blood
for Three Hours in Rabbit

MEDICAL DEVICE COMPRISING GLYCOSAMINOGLYCAN-ANTITHROMBIN III/HEPARIN COFACTOR II CONJUGATES

CROSS-REFERENCE TO RELATED APPLICATION

This application is a continuation-in-part of U.S. Ser. No. 08/564,976 filed Nov. 30, 1995.

BACKGROUND OF THE INVENTION

1. Field of the Invention

This invention relates to new chemical compounds comprising covalent conjugates of glycosaminoglycans, particularly heparins, methods for their preparation, their pharmaceutical compositions and therapeutic uses thereof.

2. Description of the Background Art

Heparin is a sulfated polysaccharide which consists largely of an alternating sequence of hexuronic acid and 2-amino-2-deoxy-D-glucose. Heparin and a related compound, dermatan sulfate, are of great importance as anticoagulants for clinical use in the prevention of thrombosis and related diseases. They are members of the family of glycosaminoglycans, (GAGs), which are linear chains of sulfated repeating disaccharide units containing a hexosamine and a uronic acid. Anticoagulation using GAGs (such as heparin and dermatan sulfate) proceeds via their catalysis of inhibition of coagulant enzymes (the critical one being thrombin) by serine protease inhibitors (serpins) such as antithrombin III (ATIII) and heparin cofactor II (HCII). Binding of the serpins by the catalysts is critical for their action and occurs through specific sequences along the linear carbohydrate chain of the glycosaminoglycan (GAG). Heparin acts by binding to ATIII via a pentasaccharide sequence, thus potentiating inhibition of a variety of coagulant enzymes (in the case of thrombin, heparin must also bind to the enzyme). Heparin can also potentiate inhibition of thrombin by binding to the serpin HCII. Dermatan sulfate acts by specifically binding to HCII via a hexasaccharide sequence, thus potentiating only the inhibition of thrombin. Since glycosaminoglycans (particularly heparin) can bind to other molecules in vivo or be lost from the site of action due to a variety of mechanisms, it would be advantageous to keep the GAG permanently associated with the serpin by a covalent bond.

Covalent complexes between ATIII and heparin have been produced previously; see, e.g., Bjork et al., (1982) *FEBS Letters* 143(1):96–100, and by Collen et al., U.S. Pat. No. 4,623,718. These conjugates required covalent modification of the heparin prior to its conjugation. The product by Bjork et al. (produced by reduction of the Schiff base between the aldehyde of a 2,5-D-anhydromannose terminus of heparin, produced by partial depolymerization of heparin to heparin fragments with nitrous acid, and a lysyl amino of ATIII) had undetectable antithrombin activity. The product by Collen et al. (produced by conjugation of carboxyl groups within the chain of the heparin molecule and lysyl amino groups of ATIII through amino-hexyl tolyl spacer arms) had a random attachment to the carboxyls of the uronic acids of the heparin moiety that might affect the ATIII binding sequence and in fact the specific anti-Xa (a coagulation protease which activates prothrombin to thrombin) activity was approximately 65% of the starting non-covalently linked unmodified heparin (*J. Biol. Chem.* 257:3401–3408 (1982)). The specific anti-thrombin activity would also be, therefore, 65% or less since both Xa and thrombin require heparin binding to ATIII. The bimolecular rate constant of the product by Collen et al. for inhibition of thrombin was claimed to be comparable to that of non-covalent mixtures of heparin saturated with ATIII (*J. Biol. Chem.* 259:5670–5677 (1984)). However, large molar excesses of heparin or covalent complex over thrombin (>10:1) were used to simplify the kinetics, which would mask the effect of any subpopulation of molecules with low activity. Specific antithrombin activities were not given.

In addition, heparin has also been covalently conjugated to other proteins (such as tissue plasminogen activator and erythropoietin) by Halluin (U.S. Pat. No. 5,308,617), using a similar method to that of Bjork et al. These conjugates suffered from the same problems associated with loss of heparin activity as with the Bjork conjugates. Coupling of heparin to affinity supports via a hydrazine linkage is reported in WO 95/05400. However, the hydrazine group is not commonly found in proteins and other macromolecules, and its incorporation often results in a decrease in biological activity. U.S. Pat. No. 4,213,962 describes heparin and antithrombin III coimmobilized on cyanogen bromide activated agarose. U.S. Pat. Nos. 5,280,016 and 4,990,502 describe the oxidation of heparin with periodate and reduction of the aldehydes so generated.

Therefore, it would be desirable to provide covalent conjugates of heparin and related glycosaminoglycans which retain maximal biological activity (e.g., anticoagulant activity) and improved pharmacokinetic properties and simple methods for their preparation. This invention fulfills these and other needs.

SUMMARY OF THE INVENTION

This invention provides a covalent conjugate comprising a glycosaminoglycan linked to another species by a covalent linkage wherein the species comprises at least one primary amino group, wherein the species is directly covalently linked via its amino group to a terminal aldose residue of the glycosaminoglycan. Preferably, the covalent linkage is an imine (>C=N–) formed between the amino group of the first species and the C1 of the terminal aldose, or the amine reduction product thereof (>CH—NH—). The glycosaminoglycan is preferably heparin or dermatan sulfate. The amine containing species may be a small molecule, such as a drug or a label, a macromolecule such as antithrombin III or heparin cofactor II, or a solid or porous or semiporous support such as is typically used in affinity chromatography.

The invention also provides novel and mild methods of preparing the above covalent conjugates which result in conjugates with improved pharmacokinetic properties and biological activity. The methods comprise incubating the glycosaminoglycans with the amine-containing species under conditions which allow imine formation between the terminal aldose residue of the glycosaminoglycan and the amine. The imine may be reduced to the corresponding amine or alternatively may be allowed to rearrange under mild conditions (Amadori rearrangement) to an α-carbonyl amine. The invention further provides pharmaceutical compositions comprising these conjugates and therapeutic uses thereof.

The invention also provides methods for reducing the thrombogenicity of a material, such as a synthetic polymer, by coating the material with the covalent conjugates of the inventions, especially the heparin-antithrombin III conjugate. Materials treated by this method are useful as medical or prosthetic devices.

BRIEF DESCRIPTION OF THE DRAWINGS

FIG. 13 shows the pharmacokinetic of ATH after intravenous injection as measured by ELISA of Plasma AT.

DESCRIPTION OF THE PREFERRED EMBODIMENT

Figure 1:
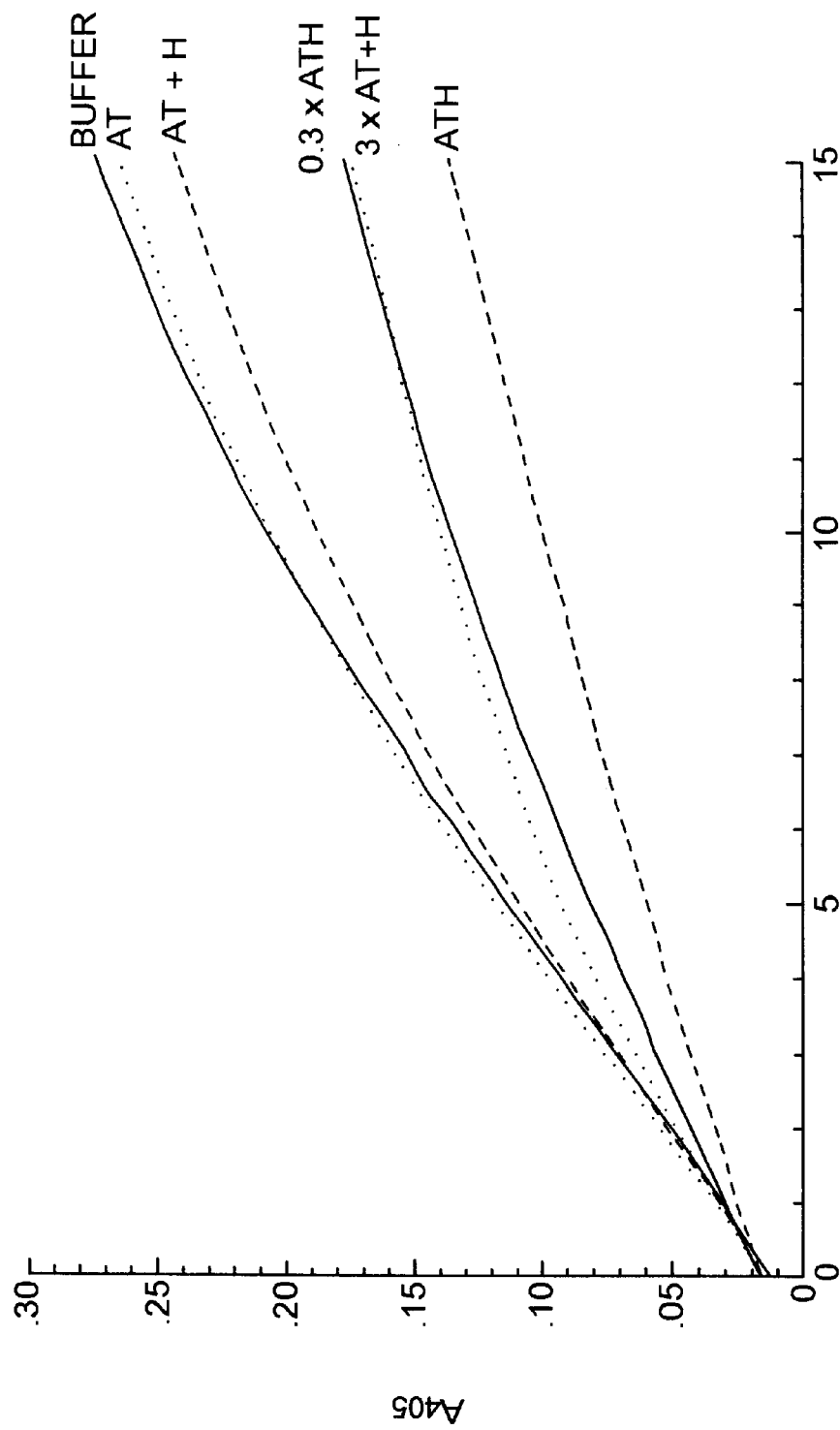
FIG. 1 compares the inhibition of thrombin activity by antithrombin III, noncovalent antithrombin III-heparin complexes and various concentrations of the covalent antithrombin III-heparin (ATH) conjugates of the present invention.

This invention provides novel covalent conjugates of glycosaminoglycans labelled at their terminal aldose residue with primary amine containing molecules. In particular, this invention provides novel covalent conjugates of heparin (Merck Index, 1980), dermatan sulfate (Tollefsen et al. (1990) *J. Biol. Chem.* 265:18263–18271) and fragments thereof with therapeutically significant serine protease inhibitors such as, for example, antithrombin III and heparin cofactor II, therapeutic uses thereof and methods for their preparation. The novel heparin conjugates of this invention are prepared under mild conditions, retain maximal anticoagulant activity compared to intact heparin, and have improved pharmacokinetic properties.

Before describing the invention in greater detail the following definitions are set forth to illustrate and define the meaning and scope of the terms used to describe the invention herein.

The term "hexose" refers to a carbohydrate ($C_6H_{12}O_6$) with six carbon atoms. Hexoses may be aldohexoses such as, for example, glucose, mannose, galactose, idose, gulose, talose, allose and altrose, whose open chain form contains an aldehyde group. Alternatively, hexoses may be ketoses such as fructose, sorbose, allulose and tagatose, whose open chain form contains a ketone group.

The term "uronic acid" refers to the carboxylic acid formed by oxidation of the primary hydroxyl group of a carbohydrate and are typically named after the carbohydrate from which they are derived. Therefore, oxidation of the C6 hydroxyl of glucose gives glucuronic acid, oxidation of the C6 hydroxyl of galactose gives galacturonic acid and oxidation of the C6 hydroxyl of idose gives iduronic acid.

The term "hexosamine" refers to a hexose derivative in which at least one hydroxy group, typically the C2 hydroxy group, has been replaced by an amine. The amine may be optionally alkylated, acylated (such as with muramic acid), typically by an acetyl group, sulfonated, (O or N-sulfated), sulfonylated, phosphorylated, phosphonylated and the like. Representative examples of hexosamines include glucosamine, galactosamine, tagatosamine, fructosamine, their modified analogs and the like.

The term "glycosaminoglycan" refers to linear chains of largely repeating disaccharide units containing a hexosamine and a uronic acid. The precise identity of the hexosamine and uronic acid may vary widely and representative examples of each are provided in the definitions above. The disaccharide may be optionally modified by alkylation, acylation, sulfonation (O- or N-sulfated), sulfonylation, phosphorylation, phosphonylation and the like. The degree of such modification can vary and may be on a hydroxy group or an amino group. Most usually the C6 hydroxyl and the C2 amine are sulfated. The length of the chain may vary and the glycosaminoglycan may have a molecular weight of greater than 200,000 daltons, typically up to 100,000 daltons, and more typically less than 50,000 daltons. Glycosaminoglycans are typically found as mucopolysaccharides. Representative examples include, heparin, dermatan sulfate, heparan sulfate, chondroitin-6-sulfate, chondroitin-4-sulfate, keratan sulfate, chondroitin, hyaluronic acid, polymers containing N-acetyl monosaccharides (such as N-acetyl neuraminic acid, N-acetyl glucosamine, N-acetyl galactosamine, and N-acetyl muramic acid) and the like and gums such as gum arabic, gum Tragacanth and the like. See Heinegard, D. and Sommarin Y. (1987) *Methods in Enzymology* 144:319–373.

The term "directly covalently linked" refers to a covalent linkage between two species accomplished without the use of intermediate spacer or linkage units. Thus, when a first molecule is referred to as being directly covalently linked to a terminal aldose residue of a glycosaminoglycan via an amino group on the first molecule, this means that the nitrogen atom of the first molecule is bonded directly to an atom of the terminal aldose residue. This bond will be a covalent bond and may be a single, double or triple bond. Therefore, one of skill in the art will understand that heparin conjugates linked to another molecule via initial attachment of spacer groups such as polymethylene diamino linkers to the heparin molecule are not contemplated by this invention.

The term "protein" includes, but is not limited to, albumins, globulins (e.g., immunoglobulins), histones, lectins, protamines, prolamines, glutelins, phospholipases, antibiotic proteins and scleroproteins, as well as conjugated proteins such as phosphoproteins, chromoproteins, lipoproteins, glycoproteins, nucleoproteins.

The term "serpin" refers to a serine protease inhibitor and is exemplified by species such as antithrombin III and heparin cofactor II.

The term "amine" refers to both primary amines, $RNH_2$, and secondary amines $RNH(R')$.

The term "amino" refers to the group $>NH$ or $-NH_2$.

The term "imine" refers to the group $>C=N-$ and salts thereof.

As used herein, the terms "treatment" or "treating" of a condition and/or a disease in a mammal, means:

(i) preventing the condition or disease, that is, avoiding any clinical symptoms of the disease;

(ii) inhibiting the condition or disease, that is, arresting the development or progression of clinical symptoms; and/or (iii) relieving the condition or disease, that is, causing the regression of clinical symptoms.

As used herein, the term "substantially pure" means, an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

The conditions and diseases treated in the present invention include myocardial infarction and a large array of thrombotic states. These include fibrin deposition found in neonatal respiratory distress syndrome, adult respiratory distress syndrome, primary carcinoma of the lung, non-Hodgkins lymphoma, fibrosing alveolitis, and lung transplants. Also, the present invention can treat either acquired ATIII deficient states such as neonatal respiratory distress syndrome, L-asparaginase induced deficiency, cardiopulmonary bypass induced deficiency and sepsis or congenital ATIII deficient states. In the case of congenital ATIII deficiency, although it is unclear from the literature if any homozygous deficient infant has ever survived to the point of birth, life threatening thrombotic complications with ATIII levels of less than 0.25 Units/ml in heterozygotes requiring ATIII plus heparin may occur in up to 1 or 2 infants per year in the U.S.A.

Other uses of the invention include covalent coating of GAGs on amine containing surfaces such as central venous lines, cardiac catheterization, cardiopulmonary bypass circuits, dialysis circuits, or other external blood contacting instruments, as well as mechanical valves, stents or any in vivo prosthesis.

The novel compounds of this invention are prepared by a simple one step process, which provides for direct covalent attachment of the amine of an amine containing moiety (such as, but not limited to, amine containing oligo(poly) saccharides, amine containing lipids, proteins, nucleic acids and any amine containing xenobiotics) to a terminal aldose residue of a glycosaminoglycan. Preferably, the amine containing moiety is a protein possessing a desirable biological activity. The mild non-destructive methods provided herein allow for maximal retention of biological activity of the protein and allow direct linkage of the protein without the need for intermediate spacer groups as follows:

The glycosaminoglycan to be conjugated is incubated with the amine-containing species at a pH suitable for imine formation between the amine and the terminal aldose or ketose residue of the glycosaminoglycan. Terminal aldose and ketose residues generally exist as an equilibrium between the ring closed cyclic hemiacetal or hemiketal form and the corresponding ring opened aldehyde or ketone equivalents. Generally, amines are capable of reacting with the ring opened form to produce an imine (Schiff base). Typically, the aldoses are more reactive because the corresponding aldehydes of the ring open form are more reactive towards amines. Therefore, covalent conjugate formation between amines and terminal aldose residues of glycosaminoglycans provides a preferred method of attaching a species containing an amine to a glycosaminoglycan.

The reaction is typically carried out at a pH of about 4.5 to about 9, preferably at about 5 to about 8 and more preferably about 7 to about 8. The reaction is generally done in aqueous media. However, organic media, especially polar hydrophilic organic solvents such as alcohols, ethers and formamides and the like may be employed in proportions of up to about 40% to increase solubility of the reactants, if necessary. Non-nucleophilic buffers such as phosphate, acetate, bicarbonate and the like may also be employed.

Optionally and preferably, the imines formed by condensation of the amines of the first species with the terminal aldose residues of the glycosaminoglycans are reduced to the corresponding amines. This reduction may be accomplished concurrently with imine formation or subsequently. A wide array of reducing agents may be used, with hydride reducing agents, such as for example, sodium borohydride or sodium cyanoborohydride being preferred. Generally, any reducing agent that does not reduce disulfide bonds can be used.

Alternatively, if reduction of the intermediate imine is not desired, the imine may be incubated for a sufficient period of time, typically about 1 day to 1 month, more typically about 3 days to 2 weeks, to allow Amadori rearrangement of the intermediate imine. The terminal aldose residues of the glycosaminoglycans conjugated by the methods provided by this invention frequently possess C2 hydroxy groups on the terminal aldose residue, i.e., a 2-hydroxy carbonyl moiety which is converted to a 2-hydroxy imine by condensation with the amine of the species being conjugated to the glycosaminoglycan. In the Amadori rearrangement, which is particularly common in carbohydrates, the α-hydroxy imine (imine at C1, hydroxy at C2) formed by the initial condensation may rearrange to form an α-keto amine by enolization and re-protonation (keto at C2, amine at C1). The resulting α-carbonyl amine is thermodynamically favored over the precursor α-hydroxy imine, thus providing a stable adduct with minimal disruption of the glycosaminoglycan chain. Thus in this embodiment, the invention provides a glycosaminoglycan covalently conjugated at the C1 of the terminal aldose residue of the glycosaminoglycan to an amine containing species via an amine linkage. If desired, the resulting conjugate may be reduced or labelled by reduction of the C2 carbonyl group with a labelling reagent such a radiolabel (e.g., $NaB^3H_4$), see, M. W. C. Hatton, L. R. Berry et al. (1980) *Analytical Biochemistry* 106:417–426, or conjugated to a second amine containing species, such as a fluorescent label.

A variety of different amine containing species may be conjugated to the glycosaminoglycans by the methods disclosed herein. Therefore, this invention provides covalent conjugates of glycosaminoglycans and a variety of other species. The primary amine may be on a small molecule, such as, for example, a drug or fluorescent or chromophoric label or a macromolecule such as, for example, a protein (antibodies, enzymes, receptors, growth factors and the like), a polynucleotide (DNA, RNA and mixed polymers thereof) or a polysaccharide. Generally, when proteins are being conjugated to glycosaminoglycans, linkage will occur through the ε-amino groups of lysine residues. Alternatively, linkage may also be accomplished via the N-terminal amine by using a pH at which the ε-amino groups are protonated. In addition, many methods are known to one of skill in the art to introduce an amine functionality into a macromolecule, see, e.g., "Chemistry of Protein Conjugation and Crosslinking", by S. Wong (CRC Press, 1991) and "The Organic Chemistry of Biological Compounds", by Robert Barker (Prentice-Hall, 1971).

In particular, the present invention can be applied to a variety of other therapeutically useful proteins where longer half-life and blood coagulation considerations are important. These include blood enzymes, antibodies, hormones and the like as well as related plasminogen activators such as streptokinase and derivatives thereof. In particular, this invention provides conjugates of heparin or dermatan sulfate with antithrombin, heparin cofactor II or analogs of heparin cofactor II, described in U.S. Pat. No. 5,118,793, incorporated by reference.

Alternatively, the amine containing species may be on a solid surface, such as polyethylene, polypropylene, cellulose, nitrocellulose, nylon, glass, glass fibers, plastic, diatomaceous earth, ceramics, metals, polycarbonate, polyurethane, polyester and the like. The surface may be a porous or semiporous matrix, a gel or a viscous liquid such as, for example, commonly found in chromatographic support media such as agarose, sepharose gels, beads and the like. Such supports with glycosaminoglycans, particularly heparin and its analogs, conjugated thereto are useful in a variety of applications such as affinity chromatography, bioseparations and solid phase binding assays. In particular, the use of heparin functional supports to purify antithrombin III is known and reported in U.S. Pat. No. 3,842,061, incorporated by reference. Numerous such amine containing solid supports and methods of derivatizing such supports to incorporate reactive amino groups therein are known to one of skill in the art. Thus, direct covalent conjugates of the terminal aldose residue of a glycosaminoglycan and any species, either known to exist presently or that may be available in the future, containing a reactive amino group are within the scope of this invention.

The methods of the present invention provide glycosaminoglycan conjugates with maximal retention of biological activity. In particular, conjugates of heparin or dermatan sulfate with either ATIII or HCII are provided which possess >60%, typically >90, more typically >95%, and most typically ≧98% of intact unconjugated heparin antithrombin activity. These conjugates have a bimolecular rate constant for thrombin inhibition of 5 to 100 fold higher, generally 8 to 20 fold higher, and typically almost 10 fold higher than the covalent conjugates reported by Collen.

The method of the present invention provides intact heparin molecules conjugated to antithrombin III or heparin cofactor II. Thus, loss of biological activity associated with fragmentation or other modification of heparin prior to conjugation is avoided. It will be apparent to one of skill in the art that the heparin conjugates of this invention retain their anticoagulant activity because of their preparation from intact heparin. Therefore, it is readily apparent that one may use the methods disclosed herein to prepare active heparin conjugates by first attaching linking groups and spacers to the species sought to be conjugated to heparin (or whatever the glycosaminoglycan being used) and subsequently attaching it to heparin. Numerous methods of incorporating reactive amino groups into other molecules and solid supports are described in the ImmunoTechnology Catalog and Handbook, Pierce Chemical Company (1990), incorporated by reference. Thereby, any species possessing reactive amino groups or capable of being modified to contain such amino groups, by any method presently known or that becomes known in the future, may be covalently conjugated to glycosaminoglycans, such as heparin, by the methods disclosed herein and all such conjugates are contemplated by this invention.

As described above, the present invention takes advantage of the fact that native (isolated from intestinal mucosa) heparin, as well as dermatan sulfate, already contains molecules with aldose termini which would exist as an equilibrium between hemiacetal and aldehyde forms, a fact apparently unrecognized and unexploited in the art. Thus, we have conjugated heparin or dermatan sulfate to antithrombin serpins by reduction of the single, Schiff base formed spontaneously between the aldose terminus aldehyde on heparin or dermatan sulfate and a lysyl amino on the serpin. The heparin or dermatan sulfate is unmodified (unreduced in activities) prior to conjugation and is linked at one specific site at one end of the molecule without any unblocked activation groups or crosslinking of the serpin. Heparin has been covalently linked to ATIII or HCII and dermatan sulfate has been covalently linked to HCII. Conjugation of other GAGs (such as heparan sulfate) to serpins or other proteins (such as albumin) is possible by this method. For example, dermatan sulfate has been conjugated to albumin using the methods disclosed herein.

In another aspect of this invention we have also produced covalent complexes by simply mixing heparin and ATIII in buffer and allowing a keto-amine to spontaneously form by an Amadori rearrangement between the heparin aldose terminus and an ATIII lysyl amino group. Thus, this invention provides methods of using the Amadori rearrangement to prepare conjugates of glycosaminoglycans to amine containing species, particularly proteins. This is a particularly mild and simple method of conjugation, hitherto unrecognized in the art for conjugating such molecules, which minimizes the modification of the glycosaminoglycan, thus maximizing the retention of its biological activity.

Another aspect of this invention provides covalent conjugates of glycosaminoglycans, particularly of heparin, end-labelled with an amine containing species at the terminal aldose residue of the glycosaminoglycan. For example, heparin and ATIII are linked directly together so that the active pentasaccharide sequence for ATIII on the heparin is in close proximity for binding. This is one of the fundamental reasons for making a covalent heparin-ATIII complex, as heparin accelerates inhibition through ATIII only if ATIII can bind the active sequence. It is notable that ATH has the unique property that the H in the conjugate stoichiometrically activates the endogenous AT while catalytically activating exogenous AT. Typically, one amine containing species will be attached to each glycosaminoglycan. However, it will be apparent that the ratio of amine containing species to glycosaminoglycan may be reduced below one by adjusting the molar ratios of the reactants or the time of the reaction.

Glycosaminoglycans are available in a variety of forms and molecular weights. For example, heparin is a mucopolysaccharide, isolated from pig intestine or bovine lung and is heterogenous with respect to molecular size and chemical structure. It consists primarily of (1–4) linked 2-amino-2-deoxy-α-D-glucopyroanosyl, and α-L-idopyranosyluronic acid residues with a relatively small amount of β-D-glucopyranosyluronic acid residues. It contains material with a molecular weight ranging from about 6,000 to about 30,000. The hydroxyl and amine groups are derivatized to varying degrees by sulfation and acetylation.

Heparin molecules can also be classified on the basis of their pentasaccharide content. About one third of heparin contains chains with one copy of the unique pentasaccharide (see, Choay, *Seminars in Thrombosis and Hemostasis* 11:81–85 (1985) which is incorporated herein by reference) with high affinity for AT, whereas a much smaller proportion (estimated at about 1% of total heparin) consists of chains which contain more than one copy of the high affinity pentasaccharide (see, Rosenberg et al., *Biochem. Biophys. Res. Comm.* 86:1319–1324 (1979) which is incorporated herein by reference). The remainder (approx. 66%) of the heparin does not contain the pentasaccharide. Thus, so called "standard heparin" constitutes a mixture of the three species, "high affinity" heparin is enriched for species containing at least one copy of the pentasaccharide, and "very high affinity" heparin refers to the approximately 1% of molecules that contain more than one copy of the pentasaccharide. These three species can be separated from each other using routine chromatographic methods, such as chromatography over an anti-thrombin affinity column (e.g., Sepharose-AT; see, e.g., Lam et al., *Biochem. Biophys. Res. Comm.* 69:570–577 (1976) and Horner *Biochem. J.* 262:953–958 (1989) which are incorporated herein by reference).

One advantage of forming a conjugate between heparin and a species containing at least one primary amino group (e.g., ATIII) using the slow glycation process disclosed herein, is the apparent selection for heparin chains having two pentasaccharides. Thus, for example, ATH prepared by the method of the invention appears to be enriched for heparin species containing two pentasaccharides. When standard heparin (containing approximately 1% of two-pentasaccharide heparin) is used as a starting material, usually more than 10% of the resulting ATH comprises two-pentasaccharide heparin, more often more than about 20%, frequently more than 35%, and often more than about 50% of the ATH comprises two-pentasaccharide heparin.

Without intending to be bound by any particular mechanism, one explanation for the apparent selection of very high affinity heparin is because the incubation mixture contains a 200-fold molar excess of heparin. During the incubation process, only heparin chains containing high affinity pentasaccharides close to a terminal aldose bind to the AT for a sufficiently long period of time to allow covalent attachment to occur. Therefore there is a selective interaction between AT and the very high affinity heparin chains.

This enrichment may account for several useful properties of ATH. The ATH of the invention activates the AT to which it is conjugated, in a stoichiometric fashion, but activates exogenous AT in a catalytic fashion. Thus, the heparin within the ATH complex acts catalytically both when ATH is administered as systemic anticoagulant and when ATH is used to coat surfaces to render them non-thrombogenic. The method of the invention produces an ATH complex with very high specific anti-factor IIa activity. In addition, the second pentasaccharide chain in the ATH complex can react with exogenous AT molecules, thereby allowing the conjugated heparin to have catalytic activity. Moreover, the heparin in the ATH complex can be orientated in such a way that the pentasaccharide is available to bind and activate circulating AT molecules when the ATH complex is bound to the prosthetic surface.

It will be appreciated that a heparin conjugate of interest (e.g., ATH) can also be produced by incubating a species containing at least one primary amino group (e.g., ATIII) with purified very high affinity heparin (i.e., containing two pentasaccharide groups) or a fraction enriched for very high affinity heparin.

Though this invention has been illustrated primarily with respect to heparin, it is apparent that all glycosaminoglycans, irrespective of their molecular weight and derivatization, may be conjugated by the methods disclosed herein, provided they possess a terminal aldose residue. Conjugates of all such glycosaminoglycans and their preparation by the methods disclosed herein are within the scope of this invention. For example, conjugates of heparin derivatized with phosphates, sulfonates and the like as well as glycosaminoglycans with molecular weights less than 6,000 or greater than 30,000 are within the scope of this invention.

In clinical practice, the novel heparin conjugates of the present invention may be used generally in the same manner and in the same form of pharmaceutical preparation as commercially available heparin for clinical use. Thus, the novel heparin conjugates provided by the present invention may be incorporated into aqueous solutions for injection (intravenous, subcutaneous and the like) or intravenous infusion or into ointment preparations for administration via the skin and mucous membranes. One skilled in the art will recognize that all forms of therapy, both prophylactic and curative, either currently known or available in the future, for which heparin therapy is indicated may be practiced with the novel heparin conjugates provided by this invention.

The heparin conjugates of this invention find particular utility in the treatment of neonatal and adult respiratory distress syndrome (RDS). In contrast to the use of noncovalent heparin-ATIII complexes, the use of the covalent heparin conjugates of the present invention prevents loss of heparin in the lung space by dissociation from ATIII. In this case, a solution of covalent complex in a physiologic buffer could be delivered as an atomized spray down the airway into the lung via a catheter or puffer. Due to its large size, ATH will remain in the alveoli for a longer period of time. ATH is also useful for treatment of idiopathic pulmonary fibrosis (more than two days).

Long term use in the circulation could be carried out by either intravenous or subcutaneous, preferably intravenous, injection of the complex in a physiologic buffer. The covalent conjugates of this invention may also be used in the treatment of acquired ATIII deficient states characterized by thrombotic complications such as cardiopulmonary bypass, extracorporeal molecular oxygenation, etc. because a longer ½ life of the covalent complex would mean fewer treatments and less monitoring. Additionally, this invention provides for prophylactic treatment of adult patients at risk for deep vein thrombosis.

The ATH conjugate of this invention has numerous advantages over uncompleted AT and SH. Since AT is covalently linked to SH, non-specific binding of ATH to plasma proteins will be less than SH, resulting in less inter-individual variation in dose response to ATH than there is to SH. The longer half-life of ATH after intravenous injection in humans means that a sustained anticoagulant effect may be obtained by administering ATH less frequently than is required for uncomplexed AT and SH. ATH is a much more effective inactivator of thrombin and factor Xa than AT, and is expected to be effective when used in much lower concentrations than AT in patients with AT deficiency. In addition, ATH can access and inhibit thrombin bound to fibrin. Finally, when linked (e.g., covalently linked) to prosthetic surfaces (e.g., endovascular grafts), ATH has shown much greater antithrombotic activity in vivo than covalently linked AT or covalently linked hirudin.

Premature infants have a high incidence of respiratory distress syndrome (RDS), a severe lung disease requiring treatment with assisted ventilation. Long term assisted ventilation leads to the onset of bronchopulmonary dysplasia (BPD) as a result of lung injury which allows plasma coagulation proteins to move into the alveolar spaces of the lung. This results in the generation of thrombin and subsequently fibrin. The widespread presence of fibrin within the lung tissue and airspaces is consistently observed in infants dying of RDS. This fibrin gel within the airspace impairs fluid transport out of the lung airspaces resulting in persistent and worsening pulmonary edema. This invention provides novel therapies for the treatment of such fibrin-mediated diseases in lung tissue by preventing intra-alveolar fibrin formation by maintaining an "anti-thrombotic environment" and/or enhancing fibrinolysis within lung tissue, thereby decreasing the fibrin load to the air spaces of the lung.

The heparin conjugates will be delivered directly to the airspaces of the lung via the airway prophylactically (before the baby takes its first breath). This ensures that the antithrombotic agent is available directly at the site of potential fibrin deposition and that the bleeding risk associated with systemic antithrombotic therapies is avoided. In addition, the antithrombotic agent will already be present in the lung prior to the start of the ventilatory support which is associated with the initial injury, i.e., unlike systemic antithrombin administration where crossing of the administered drug to the lung airspace does not occur until after lung injury. Since heparin is covalently attached to ATIII it will remain in the lung airspaces. It can also be an adjunctive therapy to the surfactants currently administered to prevent RDS and BPD. By "lung surfactant" is meant the soap-like substance normally present in the lung's airspaces whose main role is to prevent collapse of the airspace. The conjugates can also be delivered repeatedly via the endotracheal tube or as an inhaled aerosol. Adjunctive therapy can also be practiced with asthma medications by inhaler (e.g., anti-inflammatory steroids such as beclomethasone dipropionate), other anti-asthmatics such as cromolyn sodium (disodium salt of 1,3-bis(2-carboxychromon-5-yloxy)-2-hydroxypropane, INTAL®) and bronchodilators such as albuterol sulfate.

A variety of other diseases associated with elevated thrombin activity and/or fibrin deposition can be treated by administration of the conjugates of this invention. The inflammatory processes involved in adult respiratory distress syndrome are fundamentally similar to neonatal RDS and can be treated by the antithrombotic therapy described. Spontaneous lung fibrosis has also been shown to have activation of the coagulation/fibrinolytic cascades in the lung airspaces. Fibrotic disease of the lung is often a side effect associated with cancer chemotherapy and the RDS antithrombotic administration of the covalent heparin conjugates of this invention can be administered prophylactically prior to cancer chemotherapy to prevent lung fibrosis. Administration is repeated after chemotherapy in order to ensure no fibrin formation. A decrease in antithrombin III activity and an increase in thrombin activity in sepsis is also well documented. Sepsis is the most common risk factor for developing adult RDS. Thus, the heparin conjugates of this invention can be used to reduce the mortality associated with septic shock.

The conjugates of this invention are administered at a therapeutically effective dosage, i.e., that amount which, when administered to a mammal in need thereof, is sufficient to effect treatment, as described above (for example, to reduce or otherwise treat thrombosis in the mammal, or to inactivate clot-bound thrombin, or to inhibit thrombus accretion). Administration of the active compounds and salts described herein can be via any of the accepted modes of administration for agents that serve similar utilities.

The level of the drug in a formulation can vary within the full range employed by those skilled in the art, e.g., from about 0.01 percent weight (% w) to about 99.99% w of the drug based on the total formulation and about 0.01%w to 99.99% w excipient. Preferably the drug is present at a level of about 10% w to about 70% w.

Generally, an acceptable daily dose is of about 0.001 to 50 mg per kilogram body weight of the recipient per day, preferably about 0.05 to 25 mg per kilogram body weight per day, and most preferably about 0.01 to 10 mg per kilogram body weight per day. Thus, for administration to a 70 kg person, the dosage range would be about 0.07 mg to 3.5 g per day, preferably about 3.5 mg to 1.75 g per day, and most preferably about 0.7 mg to 0.7 g per day depending upon the individuals and disease state being treated. Such use optimization is well within the ambit of those of ordinary skill in the art. In the case of ATH, the long half-life allows the compound to be administered less frequently than SH (e.g., once or twice weekly).

Administration can be via any accepted systemic or local route, for example, via parenteral, intravenous, nasal, bronchial inhalation (i.e., aerosol formulation), transdermal or topical routes, in the form of solid, semi-solid or liquid dosage forms, such as for example, tablets, suppositories, pills, capsules, powders, solutions, suspensions, aerosols, emulsions or the like, preferably in unit dosage forms suitable for simple administration of precise dosages. Administration by intravenous or subcutaneous infusion is usually preferred. Most usually, aqueous formulations will be used. The conjugate is formulated in a non-toxic, inert, pharmaceutically acceptable carrier medium, preferably at a pH of about 3–8, more preferably at a pH of about 6–8. Generally, the aqueous formulation will be compatible with the culture or perfusion medium. The compositions will include a conventional pharmaceutical carrier or excipient and a conjugate of the glycosaminoglycan, and in addition, may include other medicinal agents, pharmaceutical agents, carriers, adjuvants, etc. Carriers can be selected from the various oils, including those of petroleum, animal, vegetable or synthetic origin, for example, peanut oil, soybean oil, mineral oil, sesame oil, and the like. Water, saline, aqueous dextrose or mannitol, and glycols are preferred liquid carriers, particularly for injectable solutions. Suitable pharmaceutical carriers include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in *Remington's Pharmaceutical Sciences* by E. W. Martin (1985).

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

The compounds of this invention are generally administered as a pharmaceutical composition which comprises a pharmaceutical excipient in combination with a conjugate of the glycosaminoglycan. The level of the conjugate in a formulation can vary within the full range employed by those skilled in the art, e.g., from about 0.01 percent weight (% w) to about 99.99% w of the drug based on the total formulation and about 0.01% w to 99.99% w excipient. Preferably, the formulation will be about 3.5 to 60% by weight of the pharmaceutically active compound, with the rest being suitable pharmaceutical excipients.

The compounds of the invention, particularly ATH, can be used to reduce the thrombogenicity of internal and extracorporal devices that contact blood, and find special use for coating thrombogenic prosthetic surfaces and medical devices. As used herein, "prosthetic devices" and "medical devices" refers to any natural or synthetic material that is implanted into a patient or otherwise comes into contact with blood and for which it would be desirable to reduce blood coagulation. Thus, these terms encompass endovascular tubing, arterial and central venous lines, cardiac catheters, cardiopulmonary bypass circuits, dialysis circuits, or other external blood contacting instruments, as well as pacemaker leads, arterial and venous catheters for cannulation of large vessels thrombectomy catheters, sutures, blood filters, intravenous lines, mechanical valves, stents, artificial kidneys, lungs, hearts, and livers or any in vivo prosthesis, especially those made from a natural or synthetic polymer or polymers.

Materials used in prosthetic devices include Ioplex materials and other hydrogels such as those based on 2-hydroxyethyl methacrylate or acrylamide, and poly ether polyurethane ureas (PEUU) including Biomer (Ethicon Corp.) and Avcothane (Avco-Everett Laboratories). The materials used most frequently for tubular applications are polyethylene, polypropylene, polytetrafluoroethylene (Gore-Tex), poly(vinylchloride), polydimethylsiloxane, an ethylene-acrylic acid copolymer, knitted or woven Dacron, polyester-polyurethane, polyurethane, polycarbonate-polyurethane (Corethane™), polyamide (Nylon) and polystyrene. Additional compounds used in prosthetics and biomedical devices which come into blood contact are described in Kirk-Othmer Encyclopedia of Chemical Technology, 3rd Edition 1982 (Vol. 19, pp. 275–313, and Vol. 18, pp. 219–2220) and van der Giessen et al., *Circulation* 94:1690–1997 (1996) both of which are incorporated herein by reference.

In general, the composition of the invention, e.g., ATH, will be covalently attached to the polymer of the device. Methods for covalent attachment are well known and will vary depending on the nature of the polymeric material. In general, see Hermanson, Mallia and Smith, *Immobilized Affinity Ligand Techniques,* Academic Press (1992). It will be appreciated that other polymers and materials, possibly including some not yet discovered, will be suitable for linkage to ATH or other conjugates of the invention.

In a preferred embodiment, a polyurethane-polycarbonate material is coated with ATH. This coating is carried out in three steps. First, the polymer is activated. Activation can be accomplished by treatment with an oxidant (e.g., sodium hypochlorite, NaOCl) or a reductant (e.g., Lithium Aluminum Hydride). Second, a monomer (allyl glycidyl ether) is grafted onto the surface by reacting the activated tubing with an initiator ($Na_2S_2O_4$) and a monomer (e.g., allyl glycidyl ether, acrolein, or another monomer with a functional group joined to an alkene) that can further react with the compounds of the invention, e.g., ATH. Third, the compound to be linked, (e.g., ATH or other anticoagulants that have groups, such as, an amino group, that can react with the functional group of the monomer) is linked to the monomer. One advantage of this method is that it does not involve any manipulation of ATH and does not alter its anticoagulant activity.

The conjugates of the invention are also useful as molecular weight standards for analysis of unknown samples.

Another aspect of the invention is the discovery that an Amadori rearrangement can occur spontaneously in vivo. For example, when heparin is injected into a patient, it can combine with endogenous AT to form ATH. The formation of ATH and/or HCD in vivo following heparin injection may explain, in part, some of the clinical observations of persistence of anticoagulant activity following cessation of therapy with heparin (De Swart et al., 1982, *Blood* 60:1251–58). Activated partial thromboplastin times (APTTs) in patients receiving heparin remain increased at higher values than expected, given heparin's plasma half life and the amount of drug injected. Anti-Factor Xa activity assays for heparin in humans given low molecular weight heparin intravenously still show significant plasma activity 8 h after administration of the drug has been discontinued (Dawes et al., 1986, *Haemostasis* 16:116–22).

The in vivo non-enzymatic glycation of proteins with polysaccharides most likely occurs where the two species are sequestered together, as the reaction is a time dependent and high local concentration requiring event. Potentially, any polysaccharide terminating in an aldose could undergo a spontaneous conjugation with accessible proteins. Thus, this discovery suggests that various naturally-occurring polysaccharides may become linked to protein by this mechanism. Liver glycogen is one example. Glycogen exists in both protein bound (e.g., glycogenin) and non protein bound forms (Butler et al., 1977, *Carb. Res.* 55:73–82). Protein-glycogen complexes can form by initial synthesis of a glucoside, from nucleoside sugar, using a transferase (glycogen initiator synthase). However, the present discovery suggests that alternative mechanisms involving Amadori rearrangement of aldose terminating glycogen molecules, or synthesis of glycogen from protein spontaneously glycated with maltose (or higher oligoglucosides), may also occur.

The spontaneous modification of a polysaccharide, by covalent linkage to a polypetide, would significantly change its properties. Even small amounts of these altered molecules may have important biological functions. Thus, it will useful to assay the levels of naturally occurring polysaccharide aldoses or levels of such polysaccharide-polypetide complexes, especially following administration to a patient of a compound comprising a polysaccharide terminating in an aldose, with an unsubstituted hydroxyl at $C_2$. For example, the level of ATH following heparin injection can be measured. Methods for assaying levels of a compound (e.g., ATH or other conjugates) are well known and include immunological methods such as radioimmune assays, ELISAs, and others. See, for example, Harlow and Lane, Antibodies: A Laboratory Manual, Cold Spring Harbor, N.Y. (1988) which is incorporated herein by reference.

The following examples are given to enable those of skill in the art to more clearly understand and practice the invention. They should not be considered as limiting the scope of the invention, but merely illustrative and representative thereof.

MATERIALS

In the following methodology, unless otherwise noted, "Standard heparin" refers to heparin from commercial sources. High affinity heparin is a heparin fraction in which all of the molecules bind to ATIII.

Heparin was from porcine intestinal mucosa (Sigma Chem Co U.S.A.). Dermatan sulfate was from porcine intestinal mucosa (Mediolanum farmaceutici S.p.A., Italy). ATIII was from human plasma (Bayer Inc.) HCII was from human plasma (Affinity Biologicals).

EXAMPLE I

Preparation of Covalent Conjugates between GAGs and Serpins

Reactions to form covalent complexes between the glycosaminoglycan (GAG) and serpin, for example ATIII or HCII, involved incubation of GAG (5 mg–70 mg) with the serpin (0.5 mg–3 mg) in 1 mL of sterile filtered buffer (0.3M phosphate 1M NaCl, pH 8.0 or 0.02M phosphate 0.15M NaCl, pH 7.3) containing 0.05M sodium cyanoborohydride at 35° C. to 45° C., preferably 40° C., in a sealed plastic tube (polycarbonate, polypropylene, etc). Omitting the sodium cyanoborohydride allowed formation of covalent complexes via Amadori rearrangement which could be radiolabeled by later addition of tritium labelled sodium borohydride. Incubation times ranged from 3 days to 2 weeks. Purification of the covalent product was achieved by a variety of methods. Purification procedures are described in U.S. Pat. Nos. 5,308,617, 4,623,718 and *FEBS Letters* 143(1):96–100, 1982, all incorporated by reference. Gel filtration on Sephadex G-200 using 2M NaCl produced a high molar mass fraction containing covalent complex that was essentially void of free serpin. This fraction was further purified by electrophoresis on a 7.5% polyacrylamide gel at pH 8.8 using nondenaturing conditions (no sodium dodecyl sulfate), cutting out the section of gel containing only complex and elution of the product from the cut up section of gel by incubation in buffer (3.0 g/L tris (hydroxymethyl) aminomethane 14.4 g/L glycine pH8.8) at 23 degrees C.

Alternatively, the antithrombin-heparin conjugate (ATH) was also purified in one step from the reaction mixture by hydrophobic chromatography on butyl-agarose (Sigma Chemical Company, Milwaukee, Wis.). In 2.5M ammonium sulfate, ATH and ATIII bound to butyl-agarose beads while heparin did not. Adjusting the ammonium sulfate concentration from 2.5M to 1.8M allowed pure ATH to be eluted from the beads while ATIII remained bound.

Also, ATH and ATIII bound to butyl-agarose could be eluted together by adjusting the ammonium sulfate concentration to less than 1.5M followed by separation of the ATH from ATIII on DEAE Sepharose Fast Flow beads (Pharmacia Biotech, Uppsala Sweden). ATH and ATIII eluted from butyl-agarose were dialyzed versus 0.01M Tris-HCl pH 8.0 buffer prior to binding to the DEAE beads and the bound ATIII eluted with 0.2M NaCl in buffer while ATH was eluted by NaCl concentrations of 0.4M to 2.0M. In this way, ATH of different molecular weights and charges could be isolated, depending on the NaCl concentration used. Concentration of the purified ATH was done at 4° C. by dialysis in tubing, with a 12000–14000 molar mass cut off, under nitrogen pressure (1 atmosphere).

ATH produced in 0.02M phosphate, 0.15M NaCl, 0.05M sodium cyanoborohydride pH 7.3 and purified using elution of the complex from a cut out section of gel following nondenaturing electrophoresis, yielded material in which the molar ratio of ATIII:H in the complex was 1:1.1 and >99% was active.

EXAMPLE II

Characterization of GAG-Serpin Conjugates
1. Biological Activity

Anti-Xa activity measured by Collen et al. and Bjork et al. for their respective ATH preparations was carried out by (pre)incubation of the ATH with Xa followed by determination of residual activity of Xa with S-2222 (N-benzoyl-isoleucyl-glutamyl-glycyl-arginyl-paranitroanilide (from Chromogenix, Sweden)). The percent of ATH molecules with activity (as determined by amount of Xa inhibited) is reported in Table I. Anti-IIa activity was measured for our ATH by titration with different amounts of IIa (thrombin). The amount of IIa inhibited by a given mass concentration of ATH (mass determined by analysis using unmodified starting heparin) was determined by measuring residual activity against S-2238 (D-phenylalanyl-pipecolyl-arginyl-paranitroanilide (from Chromogenix, Sweden)).
Inhibition of Thrombin Activity The inhibition of the reaction of bovine thrombin with the chromogenic substrate S-2238 was studied. All operations were carried out at 23° C. Thrombin was added, with mixing, to a solution containing the material to be tested and S-2238 dissolved in 0.036M sodium acetate 0.036M sodium barbital, 0.145M NaCl pH 7.4 buffer in an eppendorf tube (the final thrombin concentration was 0.045 I.U./ml and the final S-2238 concentration was 28.3 µg/ml). The resultant solution was transferred to a quartz cuvette and absorbance readings at 405 nm taken over time (zero time being 30 sec after addition of the thrombin). The reaction concentration of the ATIII in either the ATH, ATIII or ATIII+H (heparin) reactions was 8.8 nM. The [ATIII] in the 0.3×ATH and 3×AT+H reactions was 2.7 nM and 27 nM, respectively. In reactions where heparin was used, it was present in equimolar concentrations to the ATIII in that experiment. The results are shown in FIG. 1 and show that the ATH conjugates of the present invention are more effective than free ATIII and heparin.

Thrombin was from Parke-Davis. S-2238 was from Chromogenix (Sweden). Standard Heparin (Leo Laboratories) was used.

Reaction with Fibrinogen and Thrombin

Figure 2:
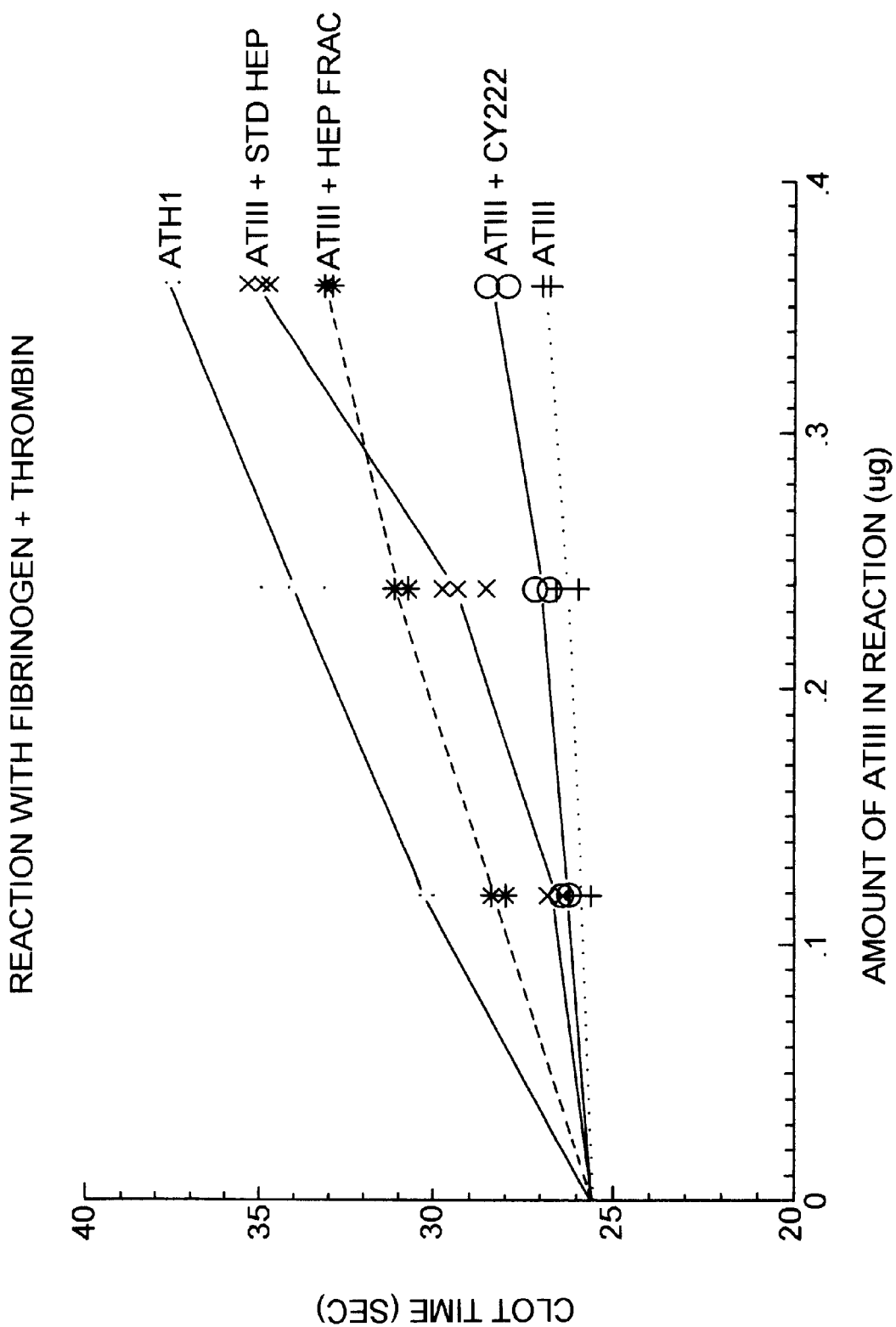
FIG. 2 shows the inhibition of the ability of thrombin to clot human fibrinogen by the covalent antithrombin III-heparin conjugates (ATH1) of the present invention.

The ability of bovine thrombin to clot human fibrinogen was inhibited by various ATIII containing mixtures as follows. An ATIII containing sample was mixed with fibrinogen in 0.15M NaCl in a plastic tube at 37° C. After 1 min, thrombin was added (the final fibrinogen concentration was 0.2 mg/ml and the final thrombin concentration was 1 I.U./ml) and a clock was started. The time was recorded for the first appearance of a clot on the end of a nichrome wire loop used for agitation. The results are shown in FIG. 2 and show that the ATH conjugates are more effective at preventing clotting. The following abbreviations are used.

ATH1=preparation #1 of ATIII-Heparin conjugate(as described in Example 1)
STD Hep=standard heparin (LEO laboratories)
HEP FRAC=low molecular weight fraction (≈7000 MW, produced by gel filtration) of standard heparin
CY222=low molecular weight heparin fragment produced by nitrous acid (average ≈2500 MW, produced by Choay Laboratories)

Thrombin was from Parke-Davis; Fibrinogen was from Connaught Laboratories. ATIII was purified from human plasma. In ATIII+heparin mixtures, the protein and GAG content were equivalent on a mass basis (only 1 in 3 standard heparin molecules bind ATIII).

Effect of added Heparin on Rate of Inhibition of Thrombin Activity by Covalent ATIII-Heparin Conjugates (ATH)

Figure 3:
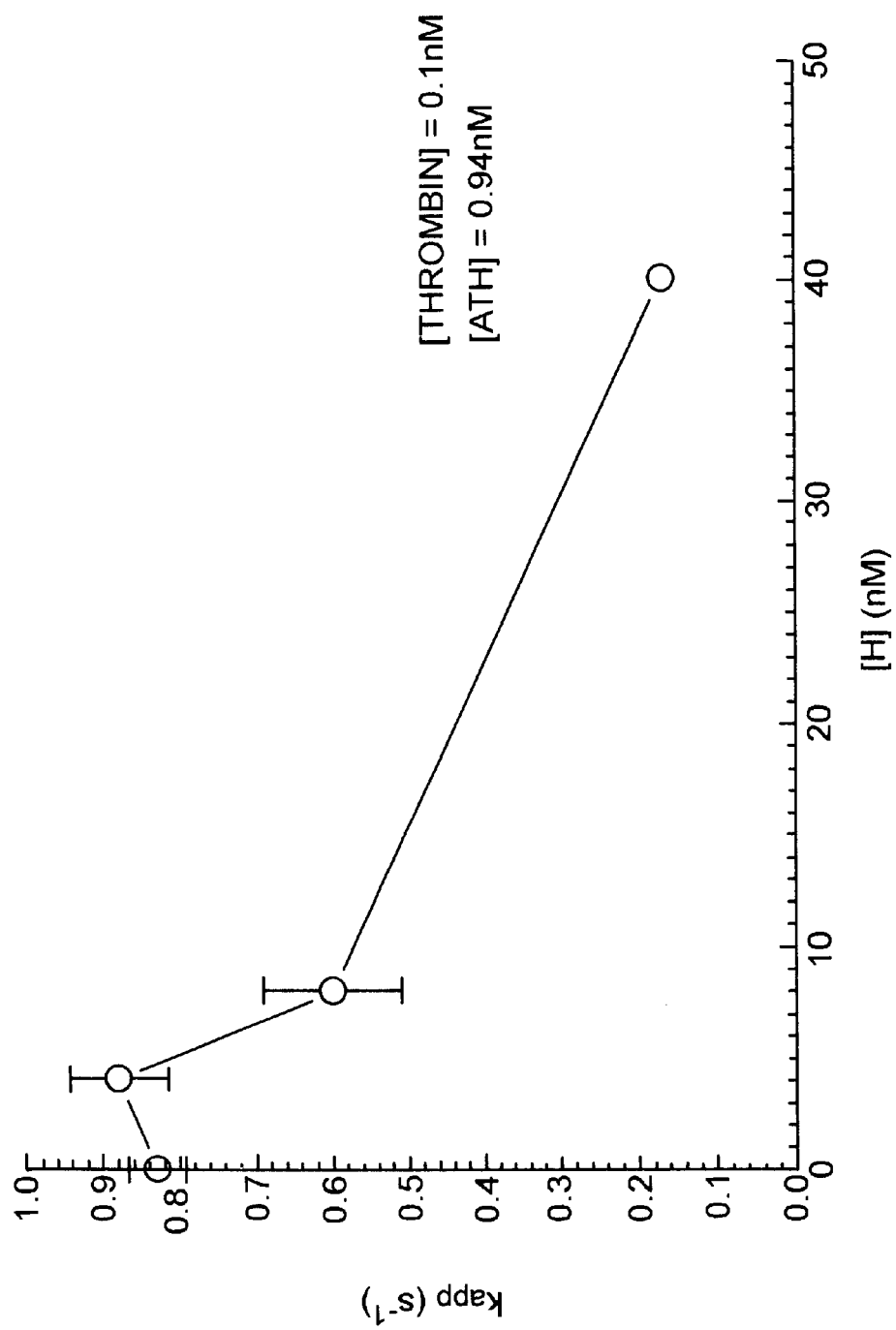
FIG. 3 shows the effect of added heparin on the rate of inhibition of thrombin by the antithrombin III-heparin conjugates of the present invention.

The ability of standard heparin to affect the inhibition of the human thrombin by ATH was tested. The buffer used was 0.1M Tris-HCl, 0.15M NaCl, 1.5 µM bovine albumin pH 7.6. ATH and varying amounts of heparin in buffer were placed in a 8 mm diameter, flat bottomed, polycarbonate, plastic tube equipped with a stirring bar rotating at 500–1000 rpm, all in a 37° C. water bath. Human thrombin was added immediately as a clock was started. After a time ranging from 0.5 to 5 sec, thrombin inhibition was stopped by addition of a solution of excess polybrene and S-2238. Residual thrombin activity for S-2238 ($A_{405}$/min) was measured in a quartz cuvette at 37° C. The results are shown in FIG. 3. A semi-log plot of residual thrombin activity (Log ($A_{405} \times 10^4$/min)) versus time (sec) was constructed for each heparin concentration used. The apparent rate constant ($k_{app}$ ($S^{-1}$)) was calculated as ln 2 divided by the time at which ½ of the starting thrombin activity was inhibited. The $k_{app}$ for each heparin concentration is plotted.

Bovine albumin was from Sigma Chemical Company, Human thrombin was from Enzyme Research Laboratories (U.S.A.), S-2238 was from Chromogenix (Sweden) and heparin was from Leo Laboratories, Canada. All concentrations quoted on FIG. 3 are reaction concentrations just prior to polybrene-S-2388 addition.

Determination of Rates of Thrombin Inhibition by ATH

Figure 4:
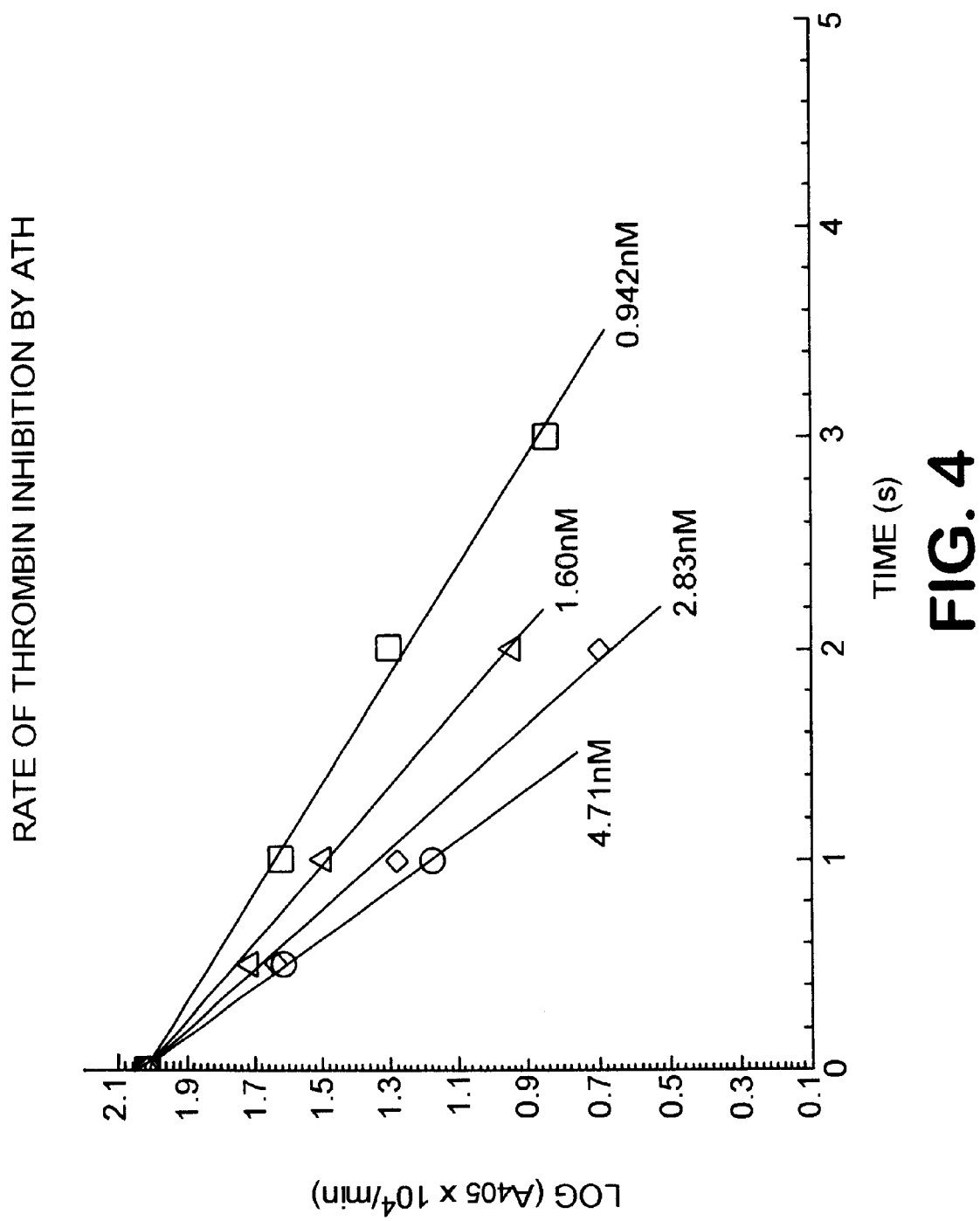
FIG. 4 shows the rate of inhibition of thrombin activity towards the chromogenic substrate S-2238 by the antithrombin III-heparin conjugates of the present invention.

The experimental procedure and calculation of the semi-log plot was the same as the experiments described above for FIG. 3 except that no exogenous heparin was added and the concentration of ATH was varied as shown. The results are shown in FIG. 4.

Inhibition of Thrombin+ATH reaction by FPR-Thrombin

Figure 5:
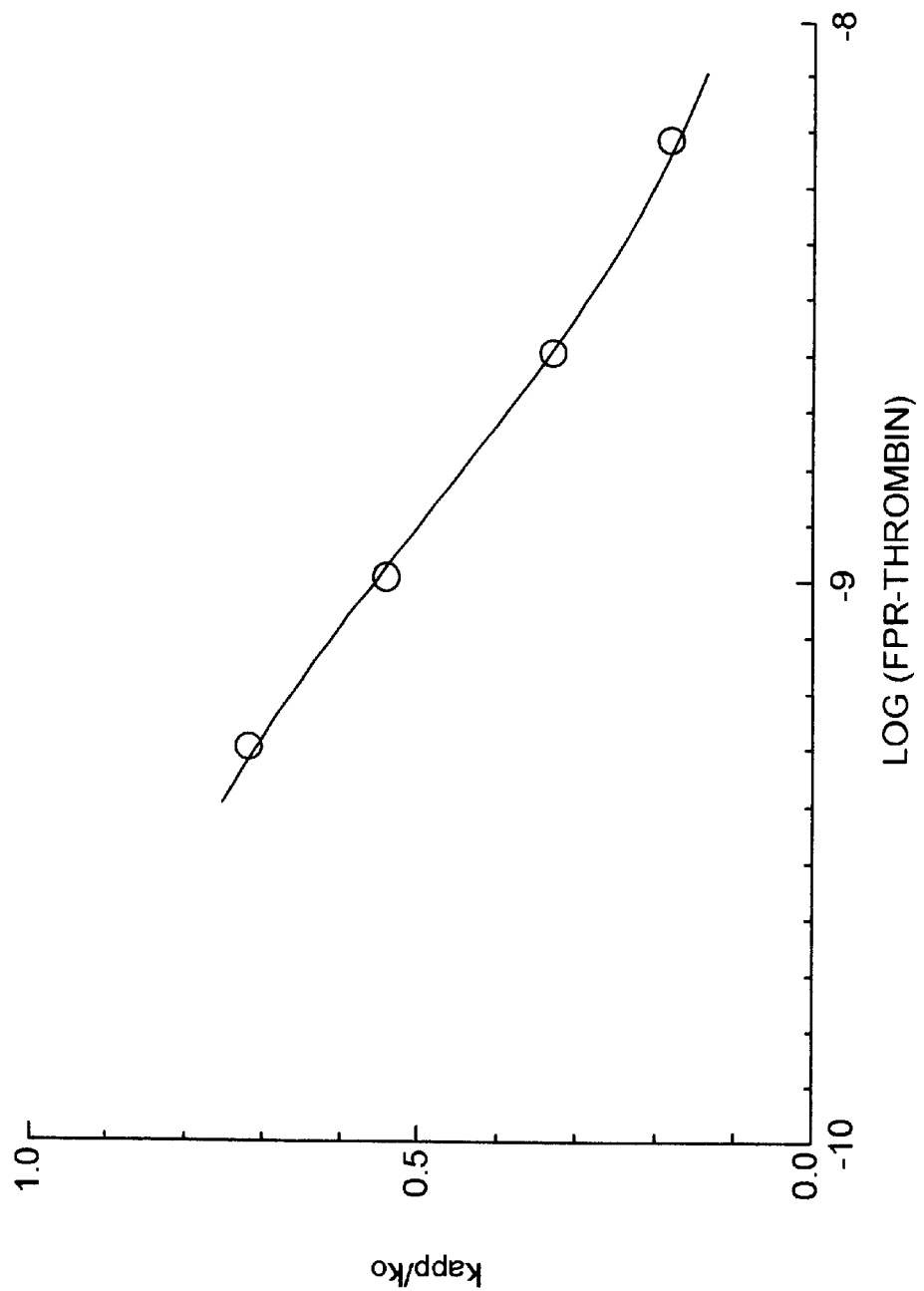
FIG. 5 shows the inhibition of the antithrombin effect of the covalent ATH conjugates of the present invention by FPR-thrombin.

FPR-thrombin is thrombin inhibited by phenylalanyl-prolyl-arginyl peptide covalently bonded to its active serine. FPR-thrombin can competitively inhibit the reaction of thrombin with ATH by binding to the heparin chain although it cannot react with the ATIII portion. The experimental procedure and calculation of $k_{app}$ was the same as for the experiments for FIG. 3 except that varying amounts of FPR-thrombin were tested instead of heparin (no exogenous heparin added). The constant $k_o$ was the $k_{app}$ value with no FPR-Thrombin added. Results are shown in FIG. 5.

Bimolecular and 2nd order rate constants and effect of added Heparin on Rate of Inhibition of Thrombin by ATH The procedure for the results for added heparin are given as determined from the results used for FIG. 3. To determine the rate constants, the method of Hoylaerts et al. in *J. Biol. Chem.* 259(9):5670–5677 (1984) was used. To calculate the bimolecular rate constant, $k_2$ and $K_i$ were determined as follows. The $k_{app}$ values for each curve for each ATH concentration used were determined for 3 separate experiments, of which FIG. 4 is a typical example. For each experiment, a plot of $1/k_{app}$ versus $1/[\text{ATH}]$ was constructed. The intercept of the $1/k_{app}$ axis was equal to $1/k_2$ and the intercept of the $1/[\text{ATH}]$ axis was equal to $1/K_i$. In each case, the bimolecular rate constant was calculated as $k_2/K_i$ and the average of 3 experiments is reported. For the second order rate constant ($k_1$), $k_{-1}$(off rate), or $IC_{50}$ for FPR-thrombin competition ([FPR-Thrombin] at which $k_{app}/k_0 = 0.5$) was determined for each curve for each of 3 experiments, of which FIG. 5 is a typical example. The averages, for the three $k_2$ and $K_i$ values measured were used to calculate the second order rate constant for each $k_{-1}$ value, given the following formula. Second order rate constant=$k_1=(k_{-1}=+k_2)/K_i$. The average is reported. Results are shown in Table 2. Error values are expressed as ±2 times the standard error of the mean.

TABLE 2

| PRODUCT | BIMOLECULAR RATE CONSTANT ($M^{-1}s^{-1}$) | 2nd ORDER RATE CONSTANT ($M^{-1}s^{-1}$) | EFFECT OF >10 FOLD MOLAR EXCESS ADDITION OF HEPARIN |
|---|---|---|---|
| BERRY et al. | $1.3 \times 10^9 \pm 2 \times 10^8$ | $3.1 \times 10^9 \pm 4 \times 10^8$ | INHIBITION OF ANTI-IIa ACTIVITY |
| COLLEN et al. | $3 \times 10^4$ | $6.7 \times 10^8$ | ANTI-Xa ACTIVITY DOUBLED |
| BJORK et al. | — | — | |

Pharmacokinetics of Covalent ATIII-Heparin Conjugates

1. Plasma Clearance of ATH and Heparin After Intravenous Injection in Rabbits

Figure 6:
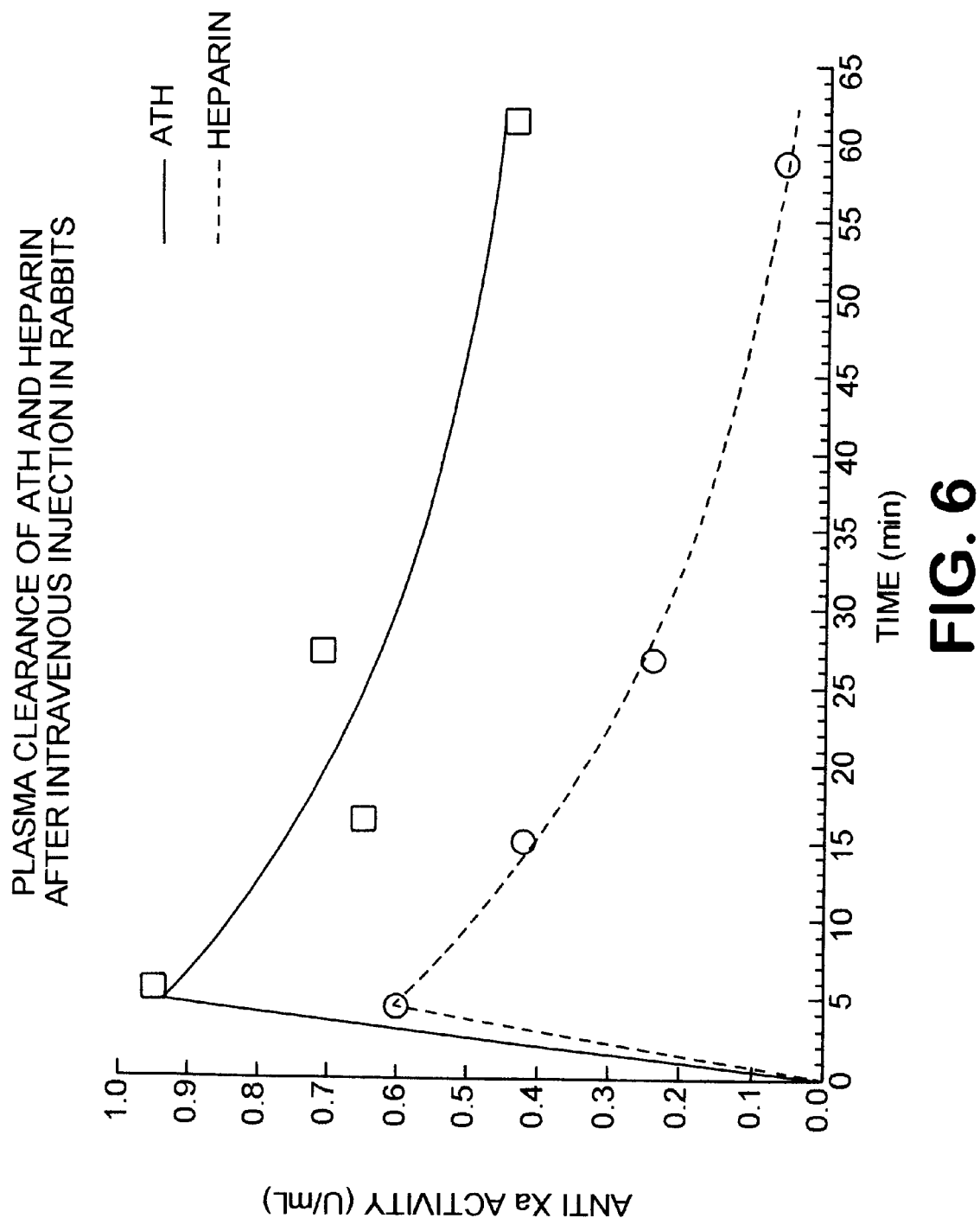
FIG. 6 shows the plasma clearance of the covalent ATH conjugates of the present invention and heparin in rabbits after intravenous injection.
Figure 7:
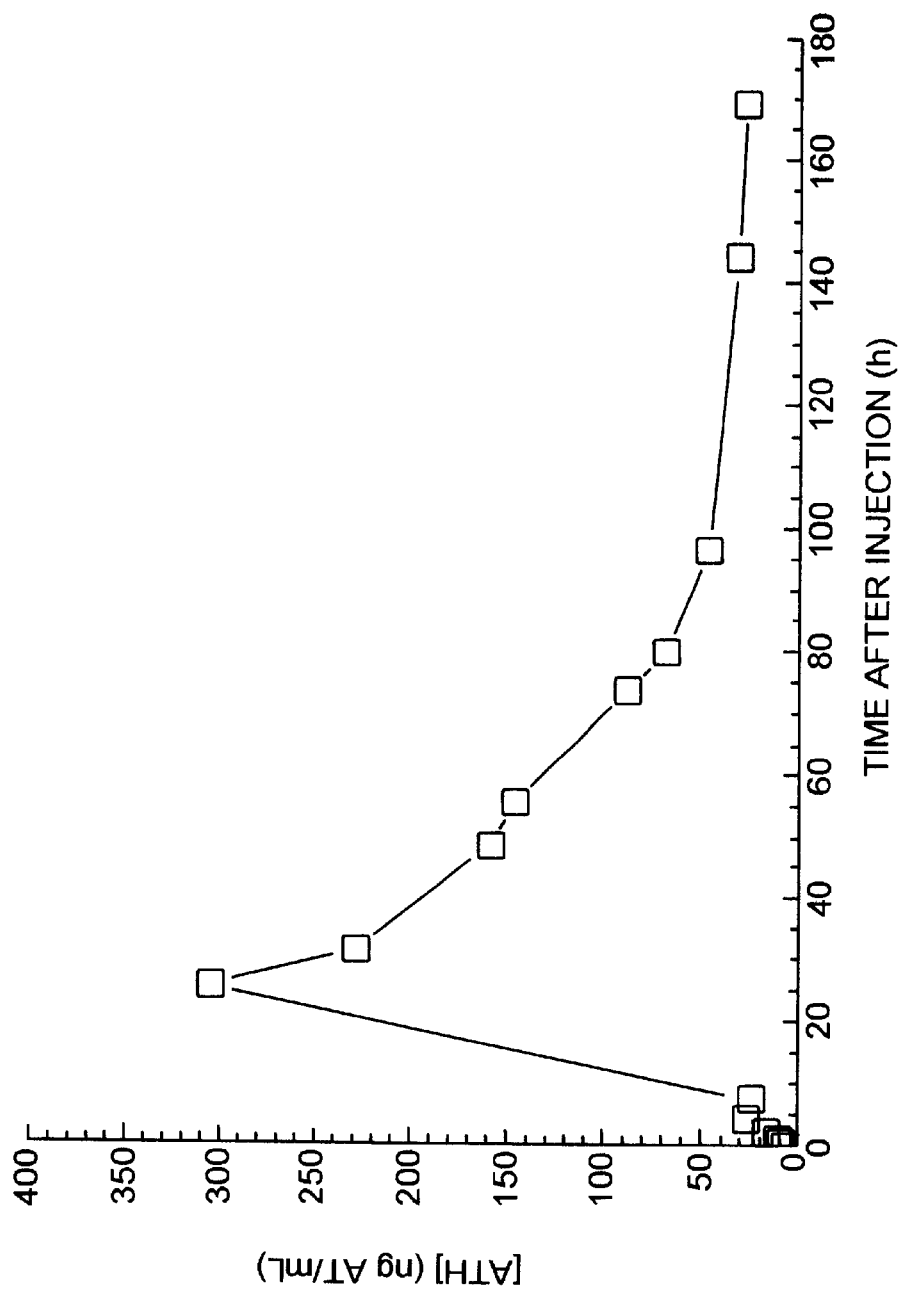
FIG. 7 shows the plasma concentrations of the covalent ATH conjugates of the present invention in rabbits after subcutaneous injection.

Purified ATH and standard heparin (Sigma) were injected into the ear vein of separate rabbits. Equivalent amounts (by mass of heparin) were injected. At various times, blood samples were withdrawn from the ear artery of each rabbit into sodium citrate (9 parts blood to 1 part 3.8% (m/v) trisodium citrate). Each sample was centrifuged at 3000 g and the resultant plasma supernatants analyzed for anti-Xa activity using an ACL300 machine (Coulter U.S.A.) for automation. The procedure employed a Stachrom Heparin kit (Diagnostica Stago, France). Briefly, each sample of plasma to be tested was mixed with buffer containing bovine ATIII and incubated with bovine factor $X_a$ at 37° C. for 30 sec followed by a 30 sec incubation with the chromogenic substrate CBS 31.39 (N-(methylsulfone)-D-leucyl-glycyl-arginyl-paranitroanilide (from Diagnostica Stago, France)), after which reaction was stopped by addition of acetic acid. The absorbance at 405 nm was then measured. A standard curve, generated using standard heparin, was used to determine the anti-$X_a$ activity in the plasma samples in terms of I.U./ml of heparin. Results are shown in FIG. 6. The ATH half life was observed to be 53 minutes and the free heparin half life was observed to be 17 minutes.

2. Pharmacokinetics in Plasma After Subcutaneous Injection in Rabbits

Figure 8:
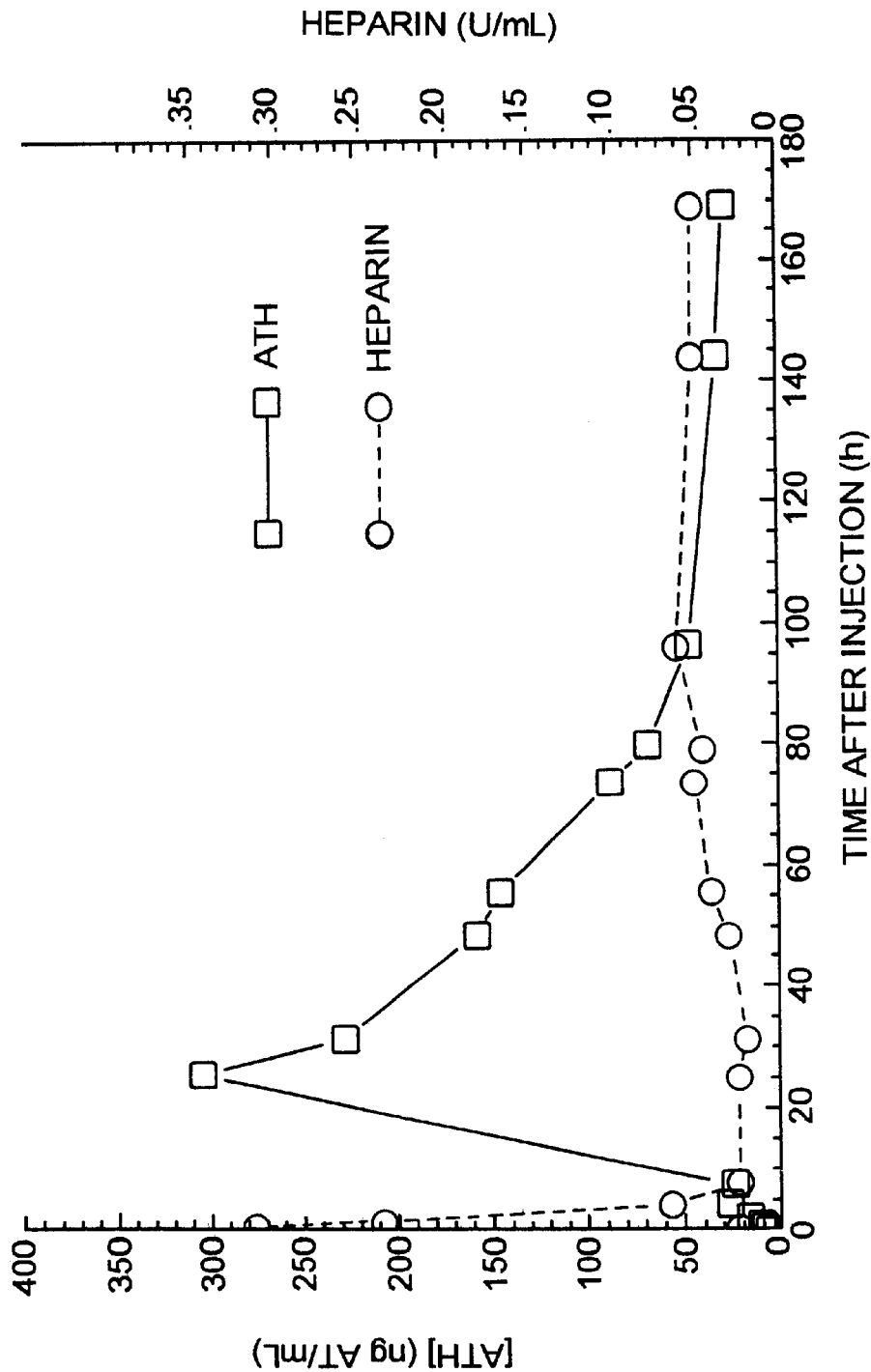
FIG. 8 shows the plasma concentrations of the covalent ATH conjugates of the present invention and heparin in rabbits after subcutaneous injection.

Rabbits were injected under the skin behind the neck and blood sampling for plasma analysis being done at various times as described above for FIG. 6. ATH was detected using an ELISA kit for ATIII from Affinity Biologicals (Hamilton, Canada). Briefly, ATH from sample plasmas was captured on plastic wells coated with sheep anti-human ATIII polyclonal antibodies. Peroxidase conjugated affinity purified anti-human ATIII antibodies (polyclonal) were applied to the wells and, after rinsing, color developed with $H_2O_2$/O-phenylenediamine substrate for 10 min. After terminating substrate reaction with $H_2SO_4$, the absorbance at 490 nm was measured. Standard curves of ATH or human ATIII in pooled normal rabbit plasma were used to determine the ng of human ATIII/ml. The rabbit's own ATIII did not interfere significantly, as the antibody used was selective for human ATIII. Results are shown in FIG. 8. In a separate experiment, when ATIII and heparin (noncovalent conjugate) was injected subcutaneously, ATIII (detected by ELISA) appeared in plasma with the same profile as ATH, but no heparin activity was observed.

2. Structural Characterization

A. General Structural Characteristics

The procedure to determine the molar ratio of Hep:AT in the heparin-antithrombin conjugates (ATH) was by densitometry of SDS gels (standard procedures) stained for either heparin (alcian blue/silver) or ATIII (Coomassie blue) compared with the corresponding standards. The activating groups per GAG molecule is by definition 1 (one aldose terminus per GAG chain).

The molecular weight range was determined from comparison of stained ATH, HCH, HCD with prestained standards on SDS polyacrylamide gels.

Characteristics of antithrombin-heparin conjugates(ATH) and heparin cofactor II-heparin (HCH) and heparin cofactor II-dermatan sulfate (HCD) conjugates are shown below in Table 1.

TABLE 1

CHARACTERISTICS OF COVALENT ATH PRODUCTS

| PRODUCT | MOLAR RATIO HEP:AT | ACTIVATING GROUPS PER HEP | MOL. WT. (SDS PAGE) | ANTI-Xa* | ANTI-IIa* |
|---|---|---|---|---|---|
| BERRY et al. | 1.1 | 1 | 69kD–100kD | | >98% |
| COLLEN et al. | 0.8–0.9 | 2.1 | | 65% | ≦65% |
| BJORK et al. | 0.7 | 1 | | 82% | UNDETECTABLE |

*ACTIVITY OF HEPARIN IN COMPLEX COMPARED TO UNMODIFIED STARTING HEPARIN

CHARACTERISTICS OF COVALENT HCH AND HCD PRODUCTS

| PRODUCT | MOLAR RATIO GAG:AT | ACTIVATING GROUPS PER GAG | MOL. WT. (SDS PAGE) | ANTI IIa* |
|---|---|---|---|---|
| HCH | 1.1 | 1 | 70kD–115kD | >90% |
| HCD | 1.4 | 1 | 78kD–150kD | >90% |

*PERCENT OF MOLECULES ACTIVE AGAINST IIa

B. Intrinsic Protein Fluorescence of ATH

Figure 24:
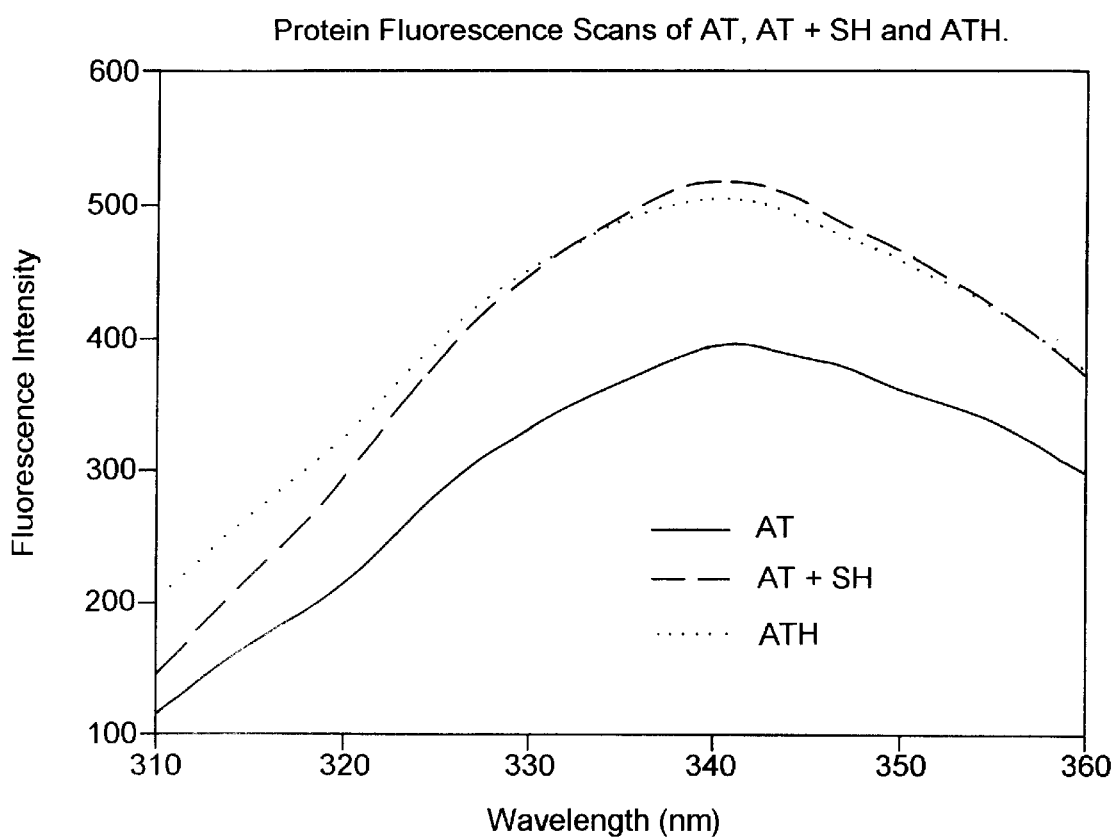
FIG. 24 shows protein fluorscence scans of AT, AT+SH, and ATH.

Since heparin is known to induce ~33% enhancement in intrinsic protein fluorescence of AT (Huntington et al (1996) Biochemistry 35,8495–8503), the intrinsic fluorescence of ATH was compared to that of AT and AT+standard heparin (SH). The protein fluorescence emission spectra of 100 nM AT, 100 nM AT plus 1277 nM SH, or 100 nM ATH were recorded ($\lambda_{ex}$ 280 nm, $\lambda_{em}$ 310–360 nm). The fluorescence of AT+H was 32% higher than that of AT alone at $\lambda_{max}$ (341 nm) with less than a 1 nm peak shift (FIG. 24). The spectrum of ATH was virtually identical to that of AT+SH. These data suggest that the conformation of ATH resembles that of the noncovalent AT-SH complex.

C. Heparin Titration of AT and ATH

Figure 25:
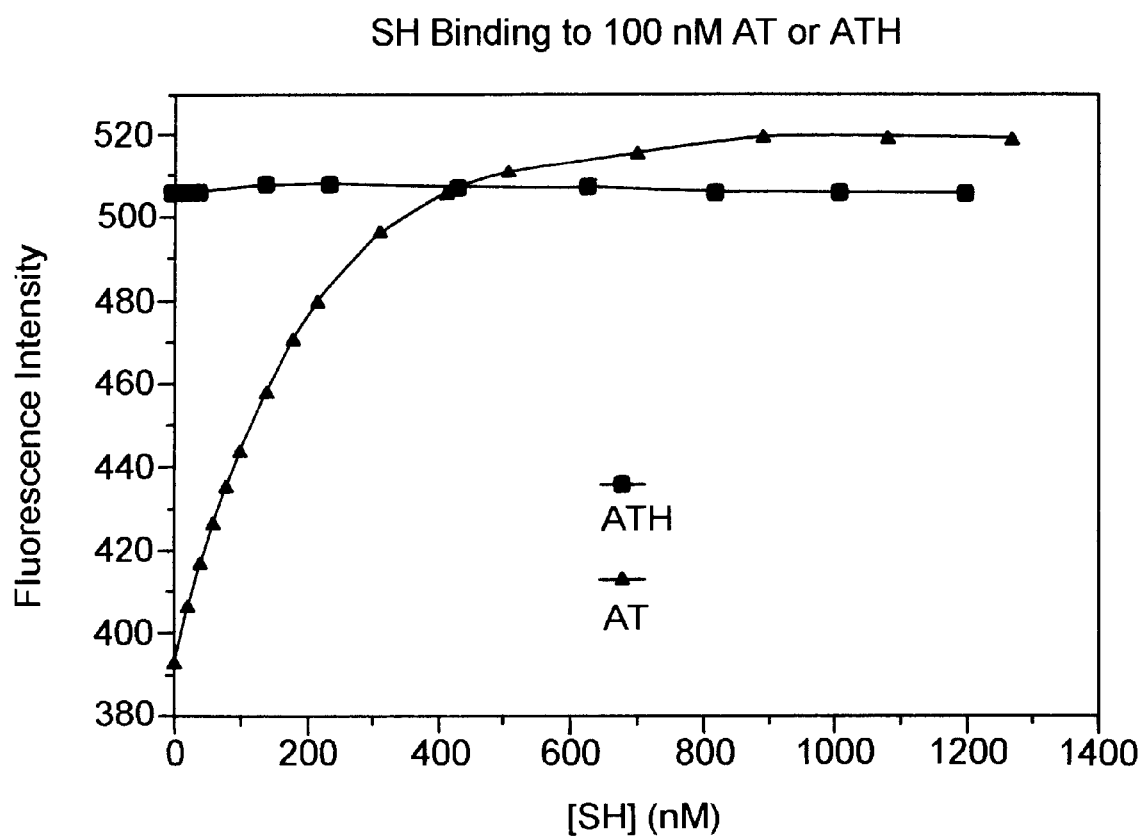
FIG. 25 shows SH binding to 100 nM AT or ATH.

A titration with SH was performed to determine whether ATH could undergo further conformational change (FIG. 25). Protein fluorescence values (at 341 nm) were determined during a SH titration of 100 nM AT and ATH. AT underwent a dose-dependent and saturable increase in fluorescent intensity that yielded a $K_d$ of 100 nM and a 32% maximal ΔFI. In contrast, there was no increase in FI with SH titration of ATH indicating no further alteration in protein conformation. Therefore, ATH is in a fully activated conformation that is independent of exogenous SH.

D. AT Titration of ATH

Figure 26:
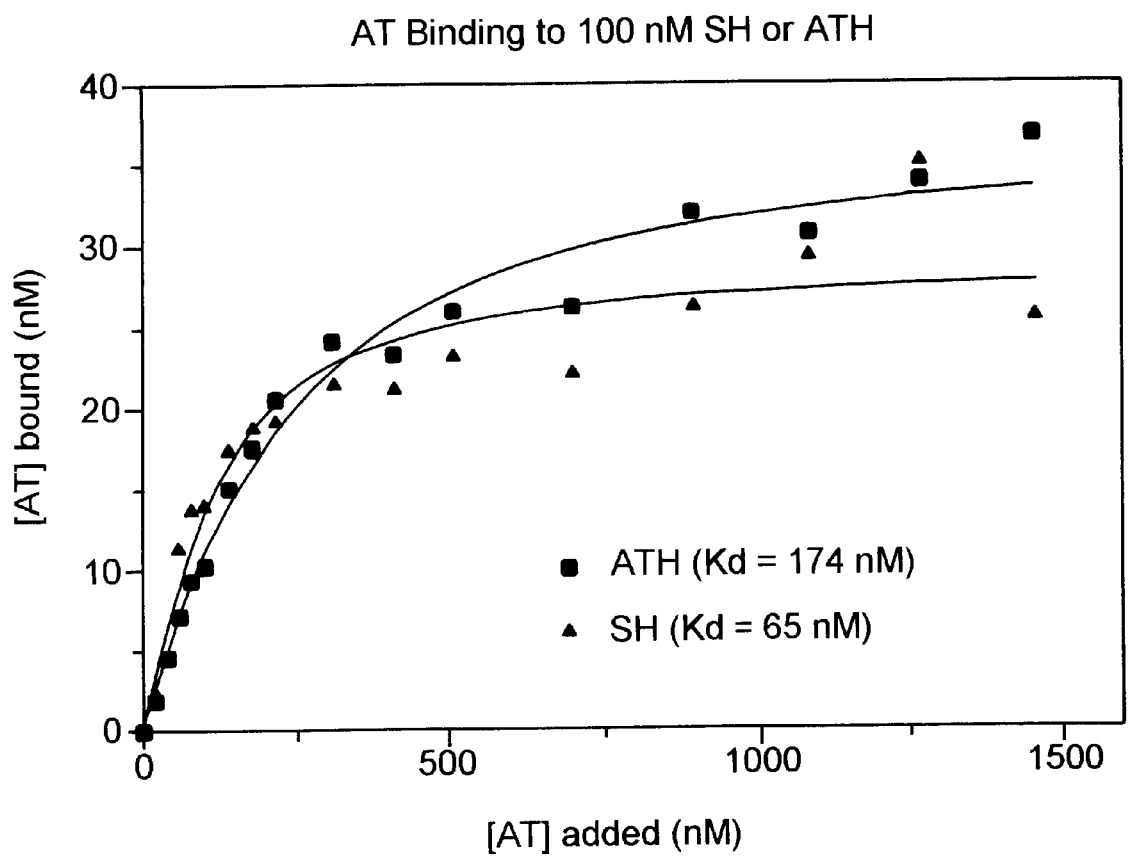
FIG. 26 shows AT binding to 100 nM SH or ATH.

In order to determine whether the heparin component of ATH was capable of binding additional AT, an AT titration of ATH was performed (FIG. 26). This was compared to an AT titration of free SH. Protein fluorescence values (341 nm) of 100 nM ATH were determined in the presence of increasing amounts of AT. The values were corrected for inner filter effect such that a control AT titration was linear. The ΔFI values were converted to AT concentration using an extinction coefficient for AT+SH determined in these studies. Binding of AT to SH and to ATH was saturable with $K_d$ values of 65 and 175 nM, respectively. The results indicate that there is 28 nM SH bound to AT in 100 nM SH, suggesting ~28% pentasaccharide content in this SH preparation. ATH is able to bind ~37 nM AT, revealing a higher pentasaccharide content. These results reveal that the heparin component of ATH is capable of binding additional AT and, therefore, is able to act catalytically.

E. Protein Conformation of ATH Compared to AT+H

In a heparin titration, the protein conformation of ATH in the absence of SH, as measured by tryptophan fluorescence, is very similar to that of AT with saturating levels of SH (FIG. 25). Therefore, within experimental error, it appears that ATH resembles SH-activated AT. Furthermore, ATH does not undergo further conformational change when SH is added suggesting that no further activation occurs. Therefore, as expected, ATH represents a fully activated form of AT that does not require exogenous SH.

F. Binding by the H in ATH of Additional AT

When AT is added to ATH there is a further increase in protein fluorescence that is due to the intrinsic H within the ATH complex. The $K_d$ of binding reveals that the affinity of H (within ATH) for AT is slightly lower than that of free SH (FIG. 26). This probably reflects competition between the covalently attached and free AT molecules. The results suggest that about 30 nM AT can bind to 100 nM SH, suggesting a pentasaccharide content of ~30%. Although the ATH -mediated binding to AT revealed higher binding, the apparent pentasaccharide content was only about ⅓ higher (~40 nM binding to AT from 100 nM ATH). This is unexpected but may be due to the competition of the AT in ATH with the exogenous AT, or that ⅓ of ATH molecules have a second pentasaccharide of the AT in ATH with the exogenous AT, or that of ATH molecules have a second pentasaccharide. These results suggest that the H within ATH is catalytic.

G. Selection for Heparin Molecules with two Pentasaccharides in Formation of ATH When a fixed amount of heparin is titrated with AT and the fluorescence intensity is monitored, there is a saturable increase in fluorescence intensity that reflects heparin-induced conformational changes in the reactive center of AT. A similar increase in fluorescence intensity is observed when ATH is titrated with AT (see FIG. 9).

Figure 9:
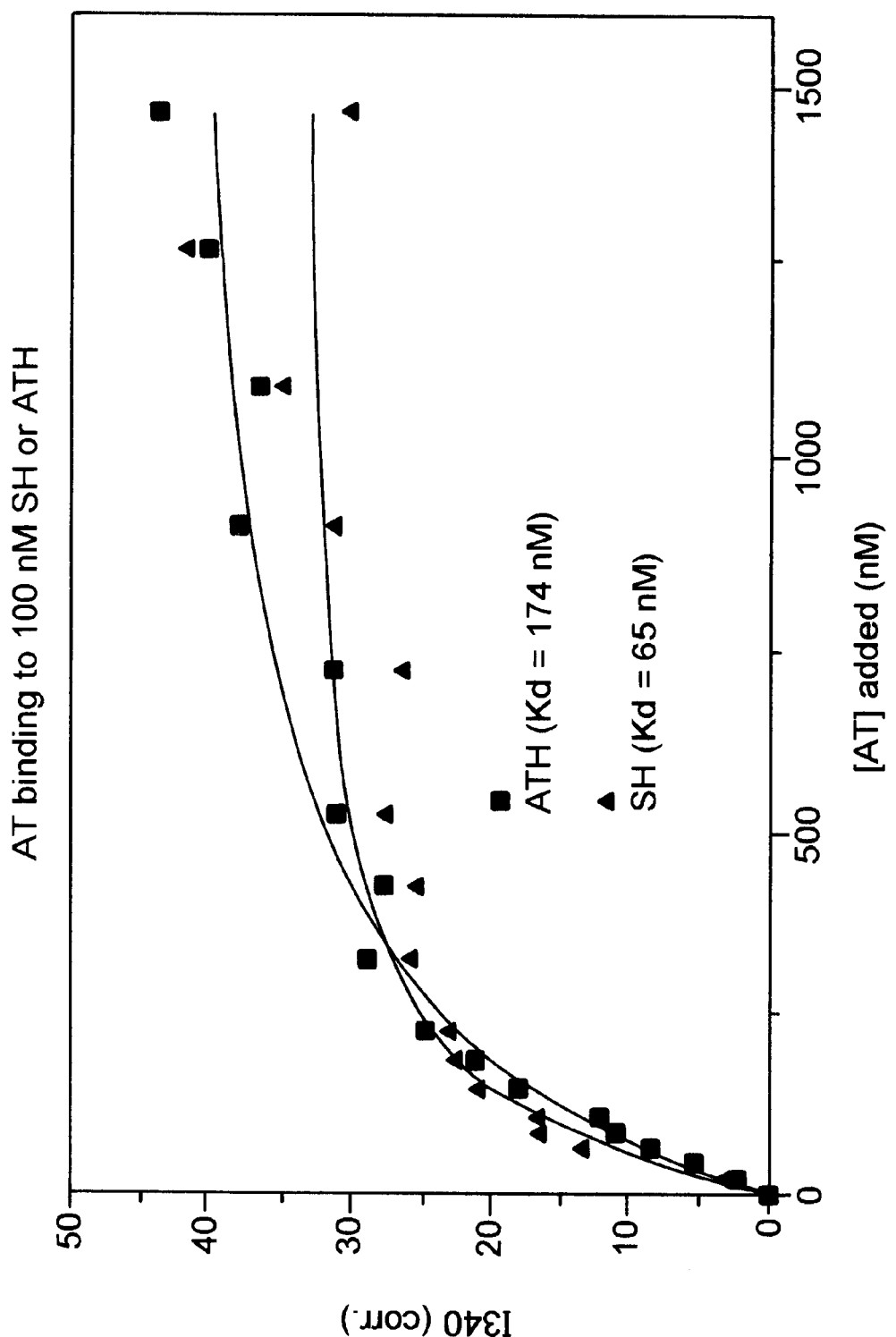
FIG. 9 shows AT binding to 100 nM SH or ATH.

The results summarized in FIG. 9, reflecting a change in fluorescence intensity that occurs when ATH is titrated with AT which is almost identical to that which occurs when heparin is titrated with AT, suggest the presence of a second pentasaccharide on the AT-conjugated heparin. This can be demonstrated by considering the result that would be expected if heparin having only one pentasaccharide were conjugated to the AT moiety of ATH. In that case, as the pentasaccharide disengaged itself from the AT to which the heparin is covalently bound, the AT would return to its native conformation, resulting in a decrease in fluorescence intensity. Once disengaged, the pentasaccharide could then bind an exogenous AT causing it to undergo a conformational change. This would be associated with a reciprocal increase in fluorescence intensity back to the starting value. The net effect of this process would be no change in fluorescence intensity, contrary to what is observed in this experiment.

EXAMPLE III

Production and Purification of ATH

Human AT (Bayer Inc.) and SH (Sigma Chem. Co. U.S.A.) were initially dialysed to ensure purity of the reagents. Human AT and SH were incubated together in a 40° C. water bath for 10–14 days. This incubation allowed the conjugation of heparin to AT by Schiff base formation between the aldose terminus aldehyde on heparin and a lysyl amino on the AT, followed by an Amadori rearrangement or reduction by sodium cyanoborohydride (final concentration 0.05M) for 5 h after the initial reaction. The sodium cyanoborohydride was added to the mixture after the incubation period. This production process is simple and does not require any structural changes to either compound.

ATH was purified using two chromatographic steps.

The first step involves adding the reaction mixture to a hydrophobic-containing matrix, butyl-agarose, in 2.5 M ammonium sulphate. Under these conditions, free AT and ATH bind to butyl-agarose beads while heparin does not. AT and ATH are than eluted off the beads by adjusting the ammonium sulphate concentration to less than 1.5 M. The ATH and AT that are eluted off the butyl-agarose matrix are then dialysed against 0.01 M Tris-HCl pH 8.0 buffer.

The second step involves applying the eluted ATH and AT onto DEAE Sepharose Fast Flow Beads in 0.2 M NaCl. Under these conditions, free AT does not bind to the DEAE Sepharose Beads. ATH is then eluted off the DEAE beads by adjusting the NaCl concentration to 2 M. The purified ATH is then concentrated by pressure dialysis at 4° C. under 1 atmosphere of nitrogen pressure in tubing with a 12000–14000 molar mass cut-off.

EXAMPLE IV

Stability of ATH

ATH was stored at 4° C. and anti-factor Xa activity assays were performed on the compound on a regular basis over 3 months. Two anti-factor Xa activity assays were used. The first had no exogenous AT added while, in the second, exogenous AT was added. Table 3 shows that the ATH lost activity after about three months.

ATH has also been stored at −70° C., with no loss of activity after six months. ATH has also been lyophilized and reconstituted with water. Prior to freeze drying, ATH was dialysed against 0.1 M Alanine and 0.15 M NaCl pH 7.0. Reconstituted ATH was active, as assayed by anti-factor Xa activity, for at least 6 months.

TABLE 3

Anti-Factor Xa Activity of ATH Over Time When Stored at 4° C.

| Date of Assay | Days After Start of Storage at 4° C. | Anti-Factor Xa Activity AT Added (u/ml) | Anti-Factor Xa Activity No AT added (u/ml) |
| --- | --- | --- | --- |
| 23.11.95 | pre | 1630 | not done |
| 11.12.95 | 5 | 1740 | 107 |
| 20.12.95 | 14 | 1760 | not done |
| 23.01.96 | 48 | not done | 62 |
| 13.03.96 | 96 | not done | 0.52 |

EXAMPLE V

Biological Activities and Mechanisms of Action of ATH

1. Direct Non-catalytic Activity

ATH has direct non-catalytic antithrombin activity as well as anti-factor Xa activity. Using a standard anti-factor Xa assay (*Thrombosis Res.* 10:399–410 (1977)) without exogenous AT added, ATH has a specific activity of 48 U/mg heparin.

Figure 10:
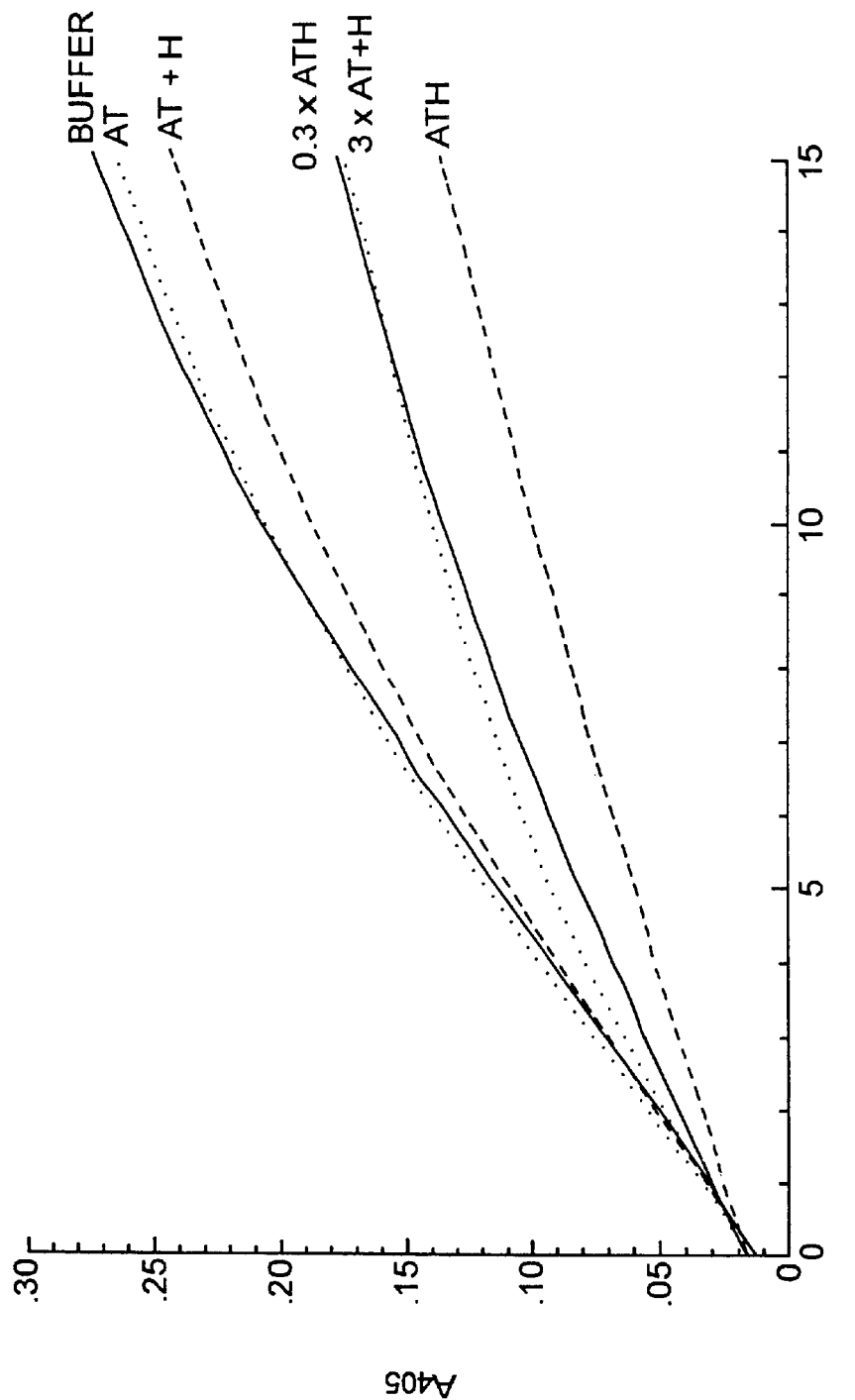
FIG. 10 shows the activity of ATH and AT+SH in inhibiting thrombin.

Inhibition of thrombin was studied by measuring the residual activity of thrombin using the chromogenic substrate S2238 (*Thrombosis Res.* 13:285–288 (1978)) after the enzyme had been reacted with ATH. The activity of ATH was compared to AT or AT+SH. The amounts of AT and or heparin used were equivalent by weight to the amounts of each used in the ATH. FIG. 10 shows that when the AT and heparin components are present in an equal mass, ATH is much more active than AT+SH in inhibiting thrombin.

2. Catalytic Activity

Figure 11:
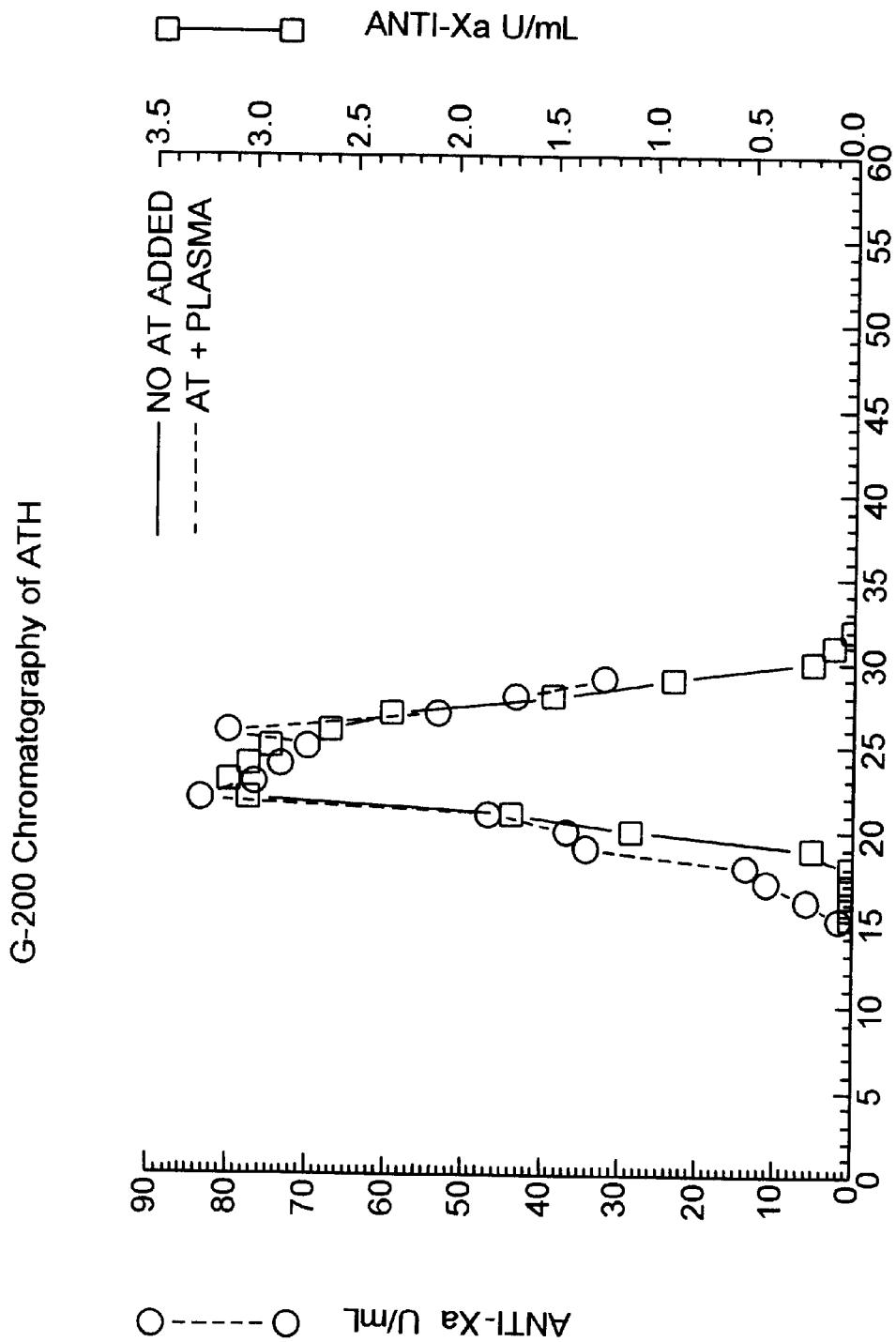
FIG. 11 shows noncatalytic [□----□] and catalytic [○----○] activities in ATH after chromotography on Sephadex G200.

The anti-factor Xa activity of ATH without exogenous AT added to the assay system was 48 u/mg. For an equivalent amount of AT, there was no measurable activity. The anti-factor Xa activity of ATH with exogenous AT added to the assay system was 731 u/mg heparin, indicating that there was catalytic activity in the ATH. Since AT is covalently linked to H in the complex, the observation that the H in ATH could catalyze AT mediated inactivation of Xa is unexpected. To rule out the possibility that the observed catalytic effect of the ATH is due to contamination of ATH with free H, ATH was subjected to gel filtration over a G-200 column. The eluted fractions were then analyzed on a 4% stacking and 7.5% separating polyacrylamide gel which clearly separates ATH from heparin. The heparin in the ATH and in the free heparin fraction was detected by alcian blue staining followed by silver nitrate and the amount of heparin in the ATH and free heparin bands was quantified using densitometry and comparing the weights of paper cut out from the area under the curves. The data are summarized in Table 4 and FIG. 11.

A fraction was selected (fraction 22) which contained 0.100818 mg H/ml as ATH and 0.498200 µg H/ml as free heparin and was assayed for anti-factor Xa activity. The specific anti-factor Xa activity of this fraction was 83.25 U/ml. If this was accounted for only by the amount of ATH present in the fraction it would be equivalent to a specific activity of 825 U/mg. If the anti-factor Xa activity in the fraction was accounted for only by the free heparin in the fraction it would require the heparin to have a specific activity of 167101 U/mg. Since the specific anti-factor Xa activity of SH is about 160 U/mg, and the amount of free heparin in the fraction is less than 0.5 µg/ml, the results of this experiment indicate that almost all of the observed anti-factor Xa activity is accounted for by ATH. The specific anti-factor Xa in this fraction (fraction 22) was assayed in the presence and absence of exogenous AT. The activity was increased 25 to 30 fold in the presence of exogenous AT. Based on the very low concentration of free heparin (described above), this fold increase could only be explained by a catalytic effect of heparin in the ATH complex. To verify this point, anti-factor Xa assays were performed in the presence of exogenous AT using heparin (high affinity) in concentration of 0.5 (the amount of free heparin in the fraction) and 5 µg/ml. In both cases, there was no measurable anti-factor Xa activity. These findings indicate that the catalytic activity observed in the ATH could not be due to contaminating free heparin, and confirm that complexed heparin in ATH has catalytic activity. The ratio of catalytic to non catalytic activity was significantly greater in high molecular weight fractions compared to low molecular weight fractions. This suggests that a higher number of pentasaccharides (i.e., two or more pentasaccharides per molecule) are present in larger ATH molecules.

TABLE 4

Anti-Factor Xa Activity of Gel Filtered ATH

| Fraction | Anti-Factor Xa Activity (u/ml) | Specific Activity of ATH if the Activity Was Due to ATH Alone (u/mg heparin) | Specific Activity of Free Heparin If the Activity Was Due to Free Heparin Alone (u/mg heparin) |
|---|---|---|---|
| 22 | 83.25 | 825.88 | 167101.6 |
| 24 | 73.26 | 634.10 | 34410.5 |
| 26 | 79.92 | 817.10 | 14468.3 |
| 28 | 43.29 | 658.10 | 4234.6 |
| 30 | 33.00 | 1005.3 | 3141.2 |

Without intending to be bound by any particular mechanism, there are two likely explanations for the observed catalytic effect of ATH.

The less likely is that when the AT component of ATH complex binds to thrombin, a conformational change occurs at the heparin binding site of AT, which results in a markedly reduced affinity for the heparin pentasaccharide. The pentasaccharide then dissociates from the AT (although the heparin molecule remains covalently linked to the AT) and is available to bind to exogenous AT.

More likely is the possibility that the process of covalent linkage of AT to heparin selects heparin molecules that contain two pentasaccharide units. Therefore, ATH can bind to AT and acts as a catalyst through the second pentasaccharide site.

In order to clarify the mechanisms responsible for the observed catalytic activity, he following experiments can be performed:

i) To differentiate between the two mechanisms, ATH will be passed over an AT column. If ATH binds to immobilized AT, it would imply that the second mechanisms is responsible. In addition the anti-factor Xa activity of ATH would be expected to be decreased by heparinase treatment if a second pentasaccharide is responsible for the increased activity.

ii) If ATH does not bind to immobilized AT it would support the first suggested mechanism as the cause of the observed catalytic effect of heparin covalently bound to AT. To evaluate this mechanism, ATH will be titrated with thrombin before passing it over an AT column. Active site-inhibited thrombin (FPR-thrombin) will be used as a control, since this does not bind to the reactive center of AT and would therefore not be expected to reduce the affinity of AT to the pentasaccharide.

3. Inactivation of ATH by Protamine

The ability of protamine sulphate and of human platelet factor 4 (PF4) to inactivate the anticoagulant activity of ATH was determined. About 80% of the anti-factor Xa activity is inactivated by either protamine sulphate or PF4. Thus, ATH activity can be neutralized during use, if necessary.

4. Rate of Inhibition of Thrombin

The second order rate constants of ATH, AT alone and AT+SH, were compared, using the method of Hoyiaerts et al. (*J. Biol. Chem.* 259(9):5670–5677). As shown in Table 5, ATH is about 30 times faster than AT+SH at inhibiting thrombin.

TABLE 5

Second Order Rate Constants for ATH

| | Second Order Rate Constants ($M^{-1}s^{-1}$) | Fold Increase Over AT Alone |
|---|---|---|
| AT | $7.0 \times 10^3$ | |
| AT + SH (saturating in AT) | $1 \times 10^8$ | 14000 |
| ATH | $3.1 \times 10^9$ | 440,000 |

5. Effect of Fibrin on Thrombin Inactivation by ATH

Thrombin bound to fibrin remains catalytically active, dissociates very slowly from fibrin, and is protected from inactivation by AT and by AT and SH. The effect of ATH on fibrin bound thrombin was evaluated and the apparent k1 of the rate of thrombin inhibition by ATH in the presence of different concentrations of fibrin monomer determined by measurement of residual thrombin at various times during the reaction. Inhibition of thrombin is stopped at various times by addition of polybrene and the thrombin activity remaining is determined using the chromogenic substrate S-2238. The results are presented in Table 6. The rate of thrombin inhibition by ATH was unaffected by fibrin monomer. In contrast, fibrin monomer decreased the ability of high affinity heparin to inhibit thrombin by about 60 fold. These results indicate that ATH can inactivate thrombin bound to fibrin.

TABLE 6

Comparison of Effect of Firbin in Monomer on Rate of Thrombin Inhibition by 100 nM ATH verses 100 nM H plus 200 mM AT

| Fibrin monomer concentration (uM) | Fold inhibition | |
|---|---|---|
| | ATH | AT + H* |
| 0.0 | 1.00 | 1.0 |
| 0.5 | 1.03 | 30.0 |
| 1.0 | 1.23 | 38.0 |
| 4.0 | 1.24 | 58.1 |

*High affinity heparin. High affinity heparin is the ATIII binding fraction of heparin purified from standard SH.

Fibrin-bound thrombin is resistant to inactivation by SH because the heparin binding site (exosite 2) on thrombin is masked when the enzyme is bound to fibrin. Since ATH can inactivate fibrin bound thrombin, experiments were preformed to determine whether exosite 2 is critical for inactivation of thrombin by ATH. These experiments were carried out using R93-thrombin, a recombinant thrombin with an inactive mutant exosite 2 (*J. Biol. Chem.* 269:17965–17970 (1994)). As shown in Table 7, ATH inactivates R93-thrombin at the same apparent rate as alpha thrombin. In contrast to ATH, the kl of high affinity heparin is about 400 times higher for alpha thrombin than for R93-thrombin. These findings suggest that exosite 2 is not required for ATH to bind to thrombin.

TABLE 7

Rate of Thrombin (IIa) Inhibition By ATH vs High Affinity Heparin (HASH)

| Type of Thrombin | Inhibitors Used | k1 (1/min) (apparent for ATH, corrected for HASH + AT) | k1(alpha IIa)/k1(R93 IIa) |
|---|---|---|---|
| alpha IIa | ATH | 3.45 | 1.0 |
| R93 IIa | ATH | 4.19 | 1.2 |
| alpha IIa | HASH + AT | 63.79 | 1.0 |
| r93 IIa | HASH + AT | 0.14 | 0.002 |

EXAMPLE VI

Pharmacokinetic Studies of ATH in Rabbits

The pharmacokinetics of ATH was studied in rabbits using anti-factor Xa assays and ELISAs for human AT. Pharmacokinetics of human AT+SH, SH alone and human AT alone in rabbits were studied for comparison with ATH.

1. Pharmacokinetics after Intravenous Administration in Rabbits

The amounts of each compound administered intravenously to rabbits were as described below. Anti-factor Xa activity was assayed by the method described in *Thrombosis Res.* 10:399–410 (1977).

|  | AT Given | Heparin Given | Anti-Factor Xa Activity Given |
|---|---|---|---|
| 1. ATH | 2.75 mg/kg | 0.698 mg/kg | 544.3 u/kg |
| 2. AT + SH | 2.75 mg/kg | 0.698 mg/kg | 124.8 u/kg |
| 3. SH |  | 0.698 mg/kg | 124.8 u/kg |
| 4. AT | 2.75 mg/kg |  |  |

Figure 12:
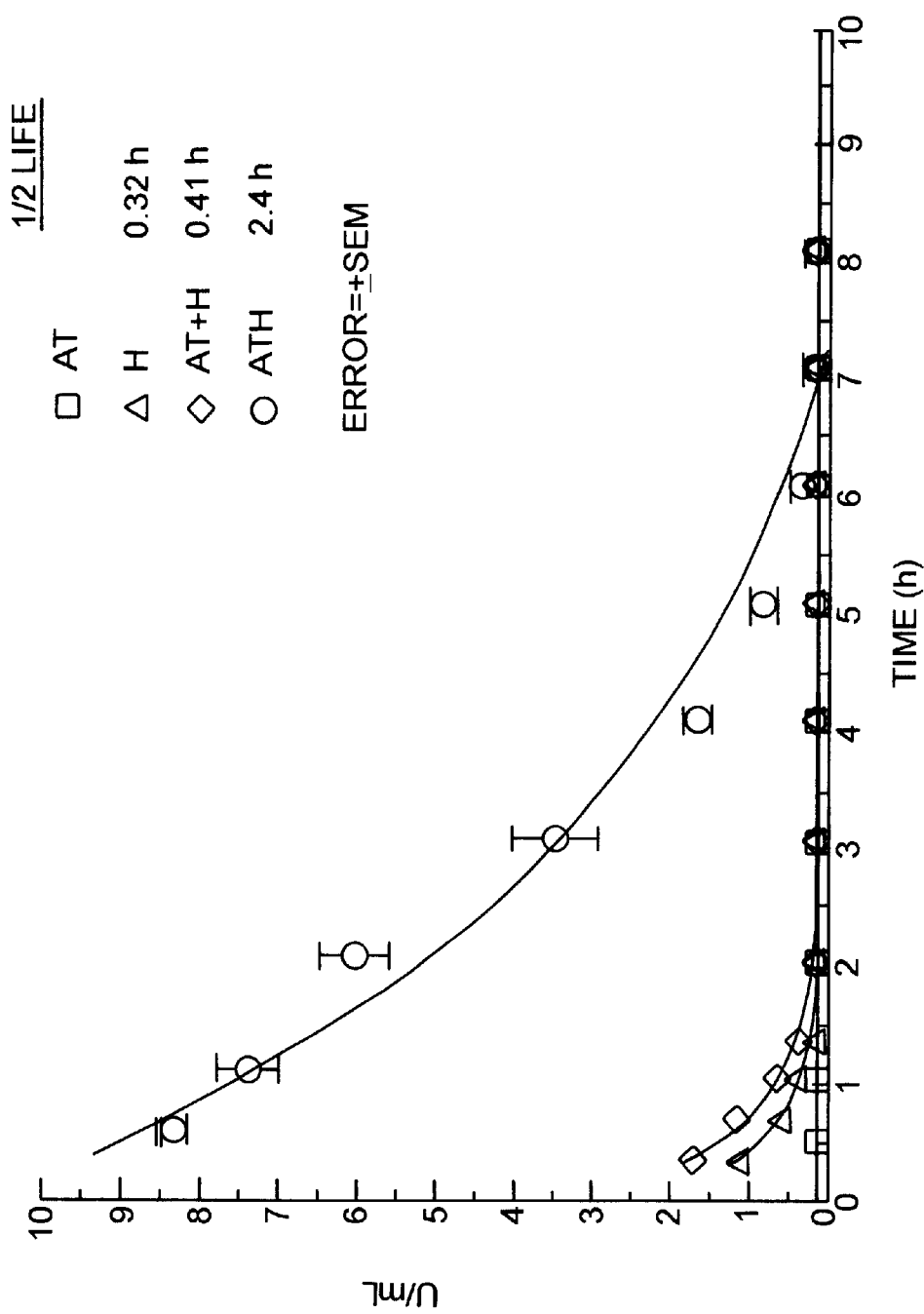
FIG. 12 shows the pharmacokinetics of ATH after intravenous injection, as measured by anti-factor Xa activity.
Figure 13:
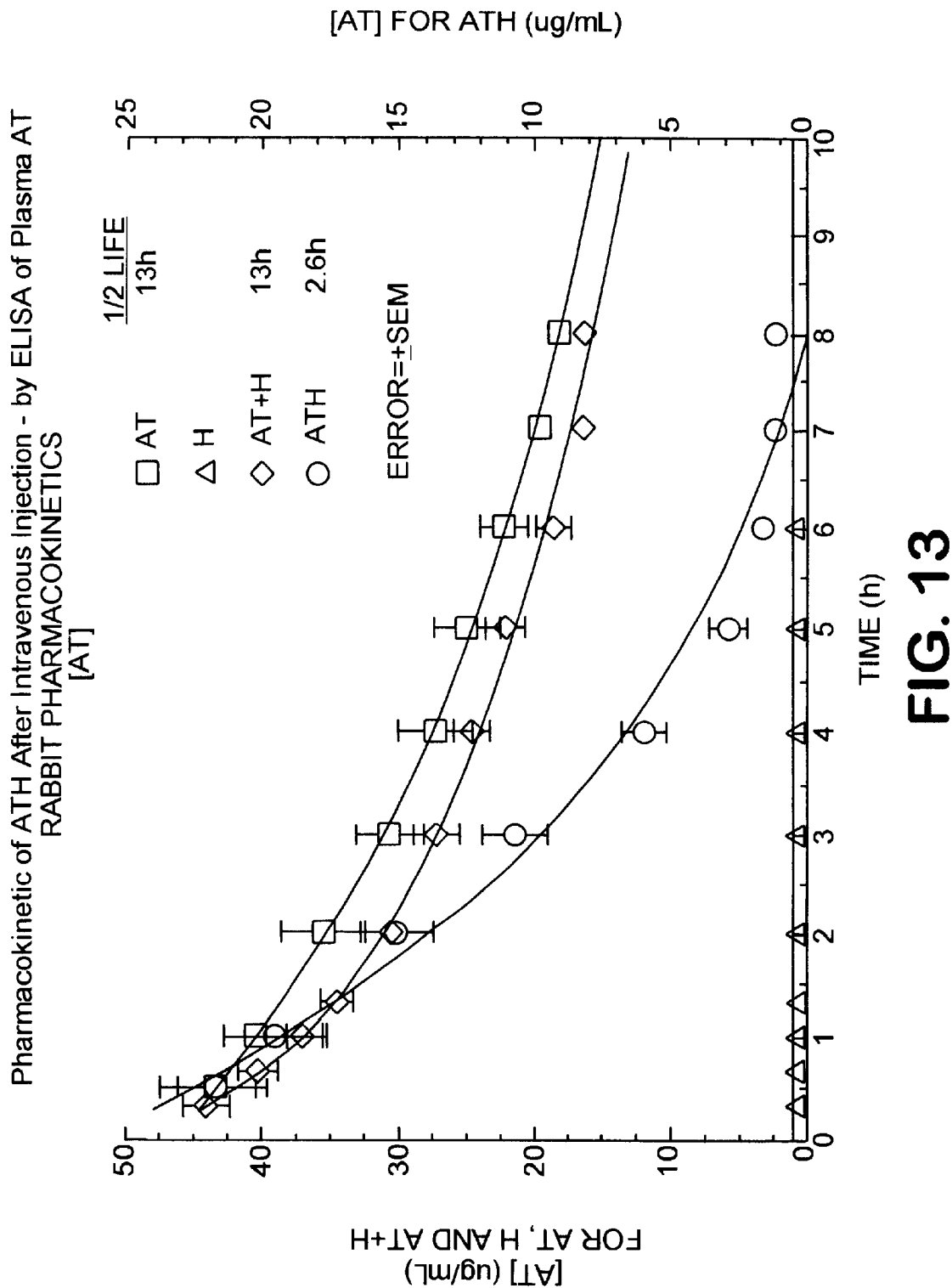

Five rabbits were used for each group. The compounds were administered intravenously to conscious, pathogen free, NZW rabbits. Citrated blood samples were taken from the rabbits at different time points up to 24 hours. Anti-factor Xa assays and ELISAs of human AT were performed on each sample. The half lives of ATH, AT+SH and SH by anti-factor Xa activity are about 2.4 hours, 0.41 hour and 0.32 hour respectively. The half lives of ATH, AT+SH and AT by ELISAs of human AT are 2.4 hours, 13 hours and 13 hours respectively. The results are summarized in FIGS. 12 and 13 and Table 8. The half lives of SH after intravenous injection and AT in humans are reported to be about 60 minutes and 66 hours respectively, which is approximately 2 times the half life of SH and 5 times the half life of AT in rabbits. Based on these observations, the half life of ATH in humans is expected to be 2–5 times that in the rabbit, which is about 5 hours to 12 hours. This long half life of ATH will be a distinct advantage for use in prophylaxis, as it can be administered infrequently. The maximal anti-factor Xa activities for ATH and SH were 8.4 u/ml and 1.17 u/ml respectively.

TABLE 8

Half Life of ATH in Rabbits

|  | t½ by Anti-Factor Xa In Rabbits | t½ by ELISA in Human AT in Rabbits | t½ Reported in Human |
|---|---|---|---|
| ATH | 2.4 hours | 2.6 hours |  |
| AT + SH | 0.41 hours | 13 hours |  |
| SH | 0.32 hours |  | 1 hour |
| AT |  | 13 hours | 66 hours |

2. Pharmacokinetics after Subcutaneous Administration in Rabbits

The amounts of compound administered subcutaneously to the rabbits were as follows:

|  | AT Given | Heparin Given | Anti-Factor Xa Activity Given |
|---|---|---|---|
| 1. ATH | 4.6 mg/kg | 1.2 mg/kg | 936 u/kg |
|  | 5.4 mg/kg | 1.7 mg/kg | 1325 u/kg |
| 2. AT + SH | 4.6 mg/kg | 1.2 mg/kg | 216 u/kg |
|  | 5.4 mg/kg | 1.7 mg/kg | 306 ug/kg |
| 3. SH |  | 1.2 mg/kg | 216 u/kg |
|  |  | 1.7 mg/kg | 306 u/kg |
| 4. AT | 4.6 mg/kg |  |  |
|  | 5.4 mg/kg |  |  |

Figure 14:
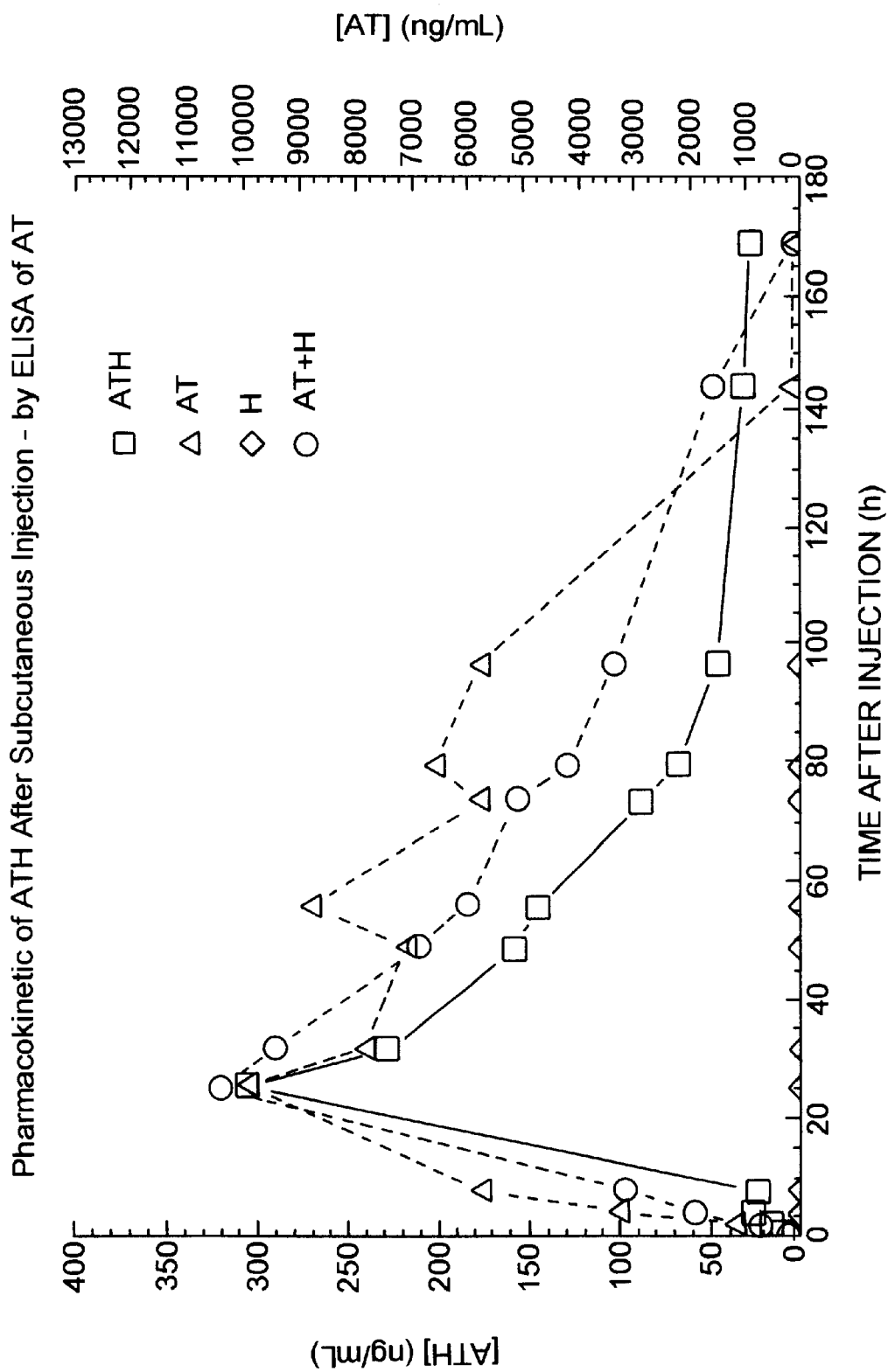
FIG. 14 shows the pharmacokinetic of ATH after subcutaneous injection.

Two dosages were tested and one animal was used for each dose. The compounds were administered subcutaneously to conscious, pathogen free, NZW rabbits. Citrated blood samples were taken from the rabbits at different time points up to 170 hours. Anti-factor Xa assays and ELISAs of human AT were performed on each sample. The maximal antifactor Xa activity for SH was 0.29 u/ml at 1 hour but there was essentially no anti-factor Xa activity in rabbits that received ATH. FIG. 14 shows the mean concentration of AT over time. These results suggested that ATH was not absorbed well with the dosage given by the subcutaneous route. This is probably due to the size of the molecule.

3. Pharmacokinetics after Tracheal Installation in Rabbits

One potential use for ATH is to treat respiratory distress syndrome. Therefore, the effect of ATH after tracheal instillation was investigated.

Figure 15:
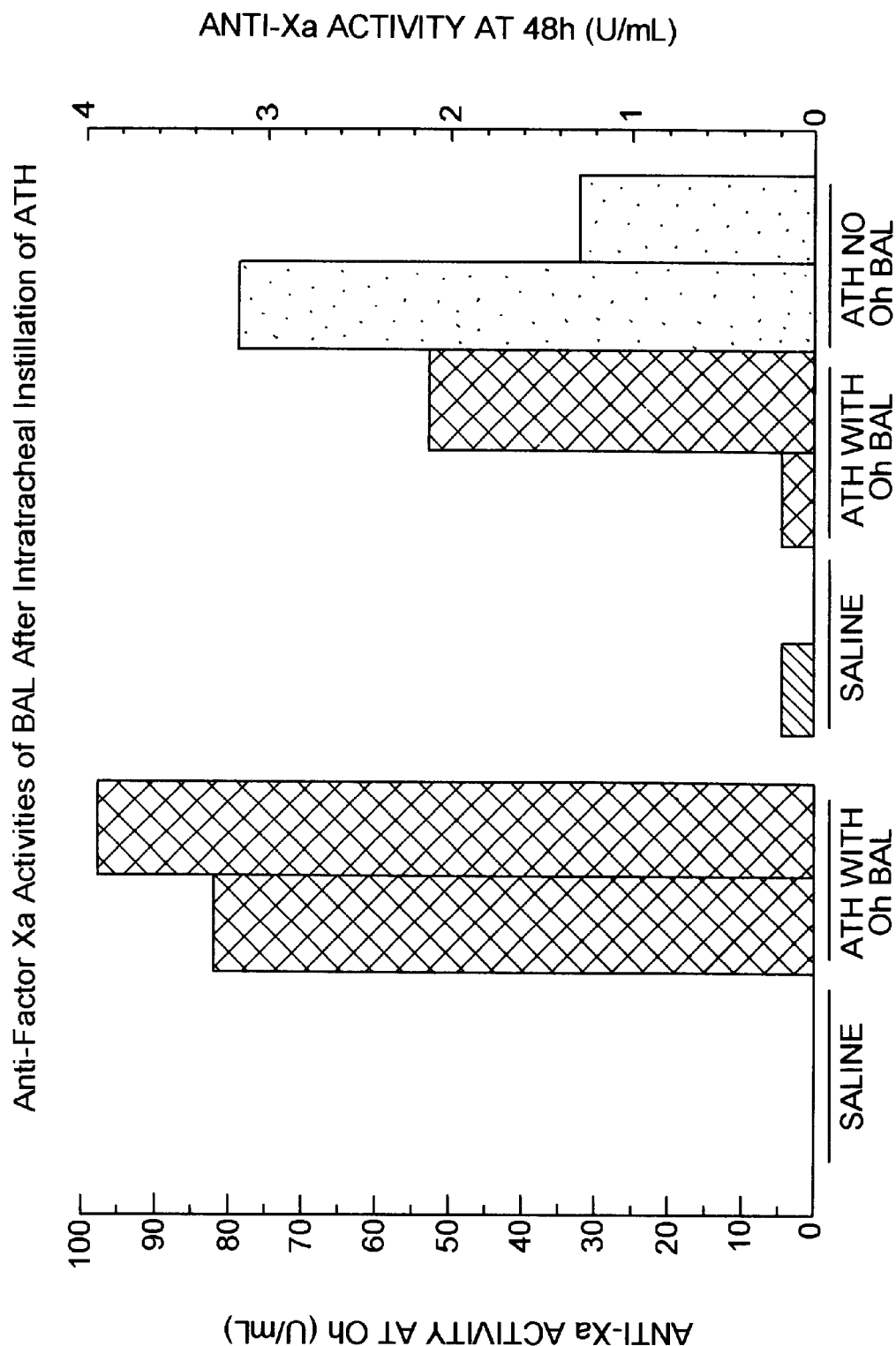
FIG. 15 shows the anti-factor Xa activities of BAL after intratracheal instillation of ATH.

ATH and saline were administered intratracheally through an endotracheal tube to anaesthetized pathogen free NZW rabbits. The amount of ATH administered was 100 anti-factor Xa u/kg. Four rabbits were used for ATH and two rabbits used for saline. For two of the rabbits that received ATH and rabbits that received saline, bronchoalveolar lavage (BAL) was done immediately after the instillation to assess whether it is possible to remove the compound after administration. BAL were collected on all animals at 48 hours. Citrated blood samples were taken at multiple time points up to 48 hours. Anti-factor Xa assays were done on both BAL and blood samples. There was essentially no anti-factor Xa activity in the blood samples. For the BAL at the time 0 hour, a significant amount of ATH was removed as evidenced by the high anti-factor Xa activity. At 48 hours, there was still anti-factor Xa activity remaining in the BAL (FIG. 15). These preliminary results demonstrated that ATH remained in the lung for a prolonged period of time and did not give rise to a significant anticoagulant effect systemically.

EXAMPLE VII

Antithrombotic and Haemorrhagic Effects of ATH in Experimental Models

Comparison with Heparin

The safety and efficacy of ATH has been tested in two animal models. The results of these experiments demonstrate that (i) ATH prevents thrombus growth and accelerates physiologic fibrinolysis in an animal model of venous thrombosis, and (ii) ATH is effective at doses that have acceptable haemorrhagic effects.

1. Comparison of ATH with Heparin in a Rabbit Bleeding Model

We compared the relative effect of ATH, AT+SH, SH alone, AT alone and saline on experimental bleeding using a rabbit bleeding ear model. The 5 treatment arms included:

|  | AT Given | Heparin Given | Anti-Factor Xa Activity Given |
|---|---|---|---|
| 1. ATH | 1.10 mg/kg | 0.279 mg/kg | 217.7 u/kg |
| 2. AT + SH | 1.10 mg/kg | 0.279 mg/kg | 49.9 u/kg |
| 3. SH | — | 0.279 mg/kg | 49.9 u/kg |
| 4. AT | 1.10 mg/kg | — | — |
| 5. Saline | — | — | — |

The doses given were equivalent by weight. Five rabbits were studied in each group.

In these experiments, rabbits were anaesthetized and test compounds were given as an intravenous bolus. Five minutes after the compounds were injected, one ear of the rabbit was punctured by a #11 surgical blade five times in a random fashion avoiding areas with visible vessels. The ear was then placed in a 37° C. water bath (total volume of 1 liter) that was stirred continuously. Ten ml aqueous samples from the water bath were taken at 5 minutes, 10 minutes, 20 minutes and 30 minutes from the time of the ear being punctured. Citrated blood samples were also taken at the same time points. Samples were centrifuged immediately at 1,700 g, platelet-poor plasma obtained and frozen at −70° C. until assays were performed.

Anti-factor Xa assays were done on the plasma samples. Absorbance of the water samples were measured at a wavelength of 540 nm and results were compared to a standard curve of known amounts of blood in water and the accumulative blood loss over time was calculated.

Figure 16:
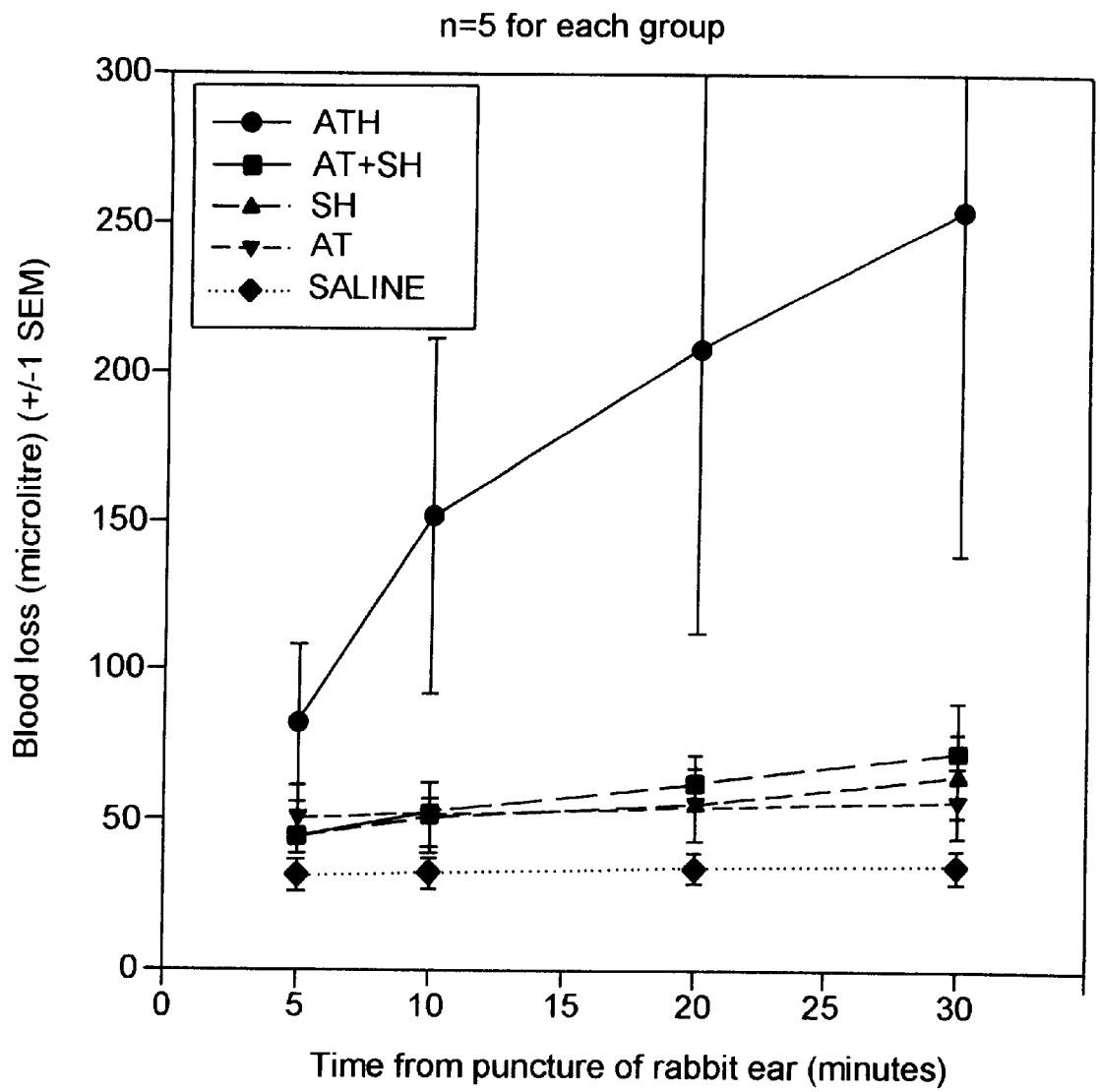
FIG. 16 shows cumulative blood loss after treatment in a rabbit bleeding ear model.
Figure 17:
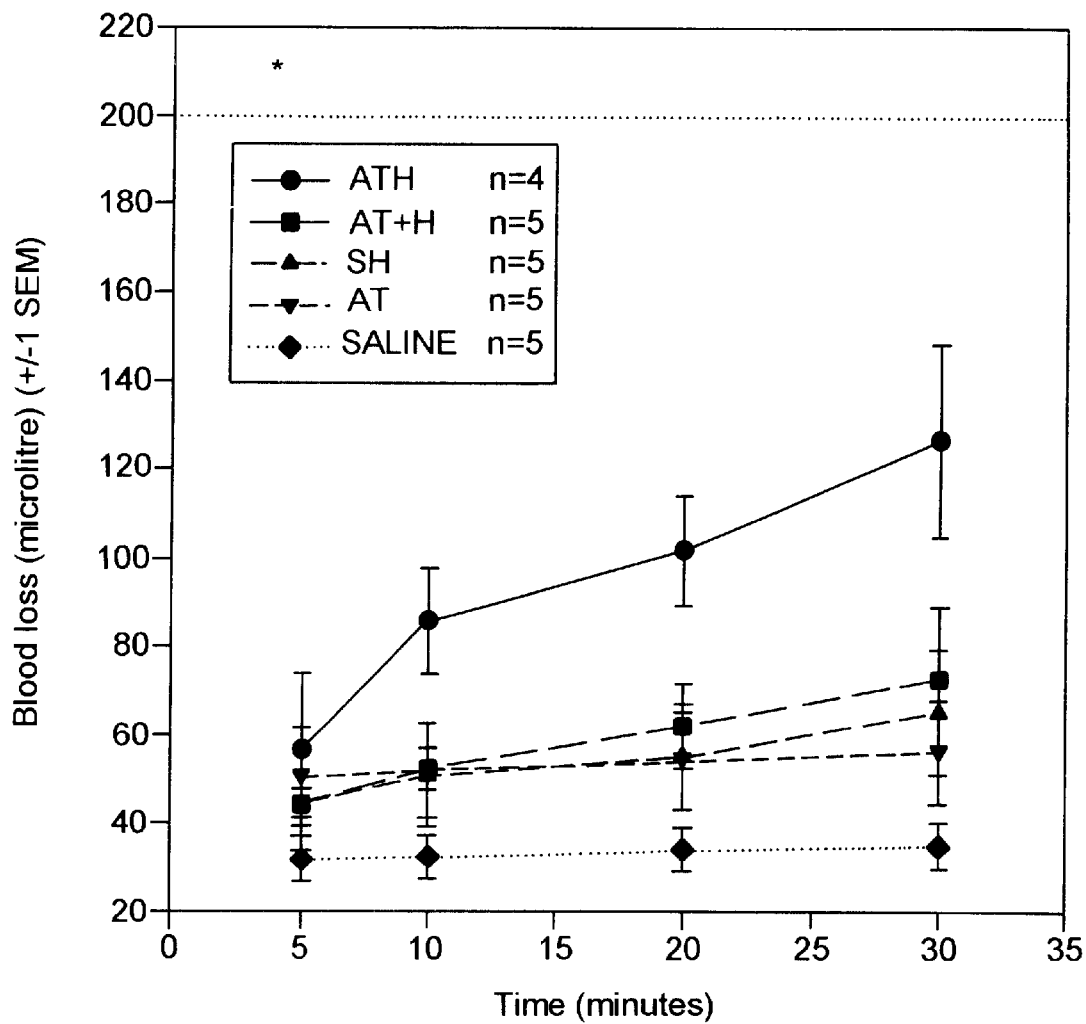
FIG. 17 shows cumulative blood loss after treatment (with outlier removed) in a rabbit bleeding ear model.
Figure 18:
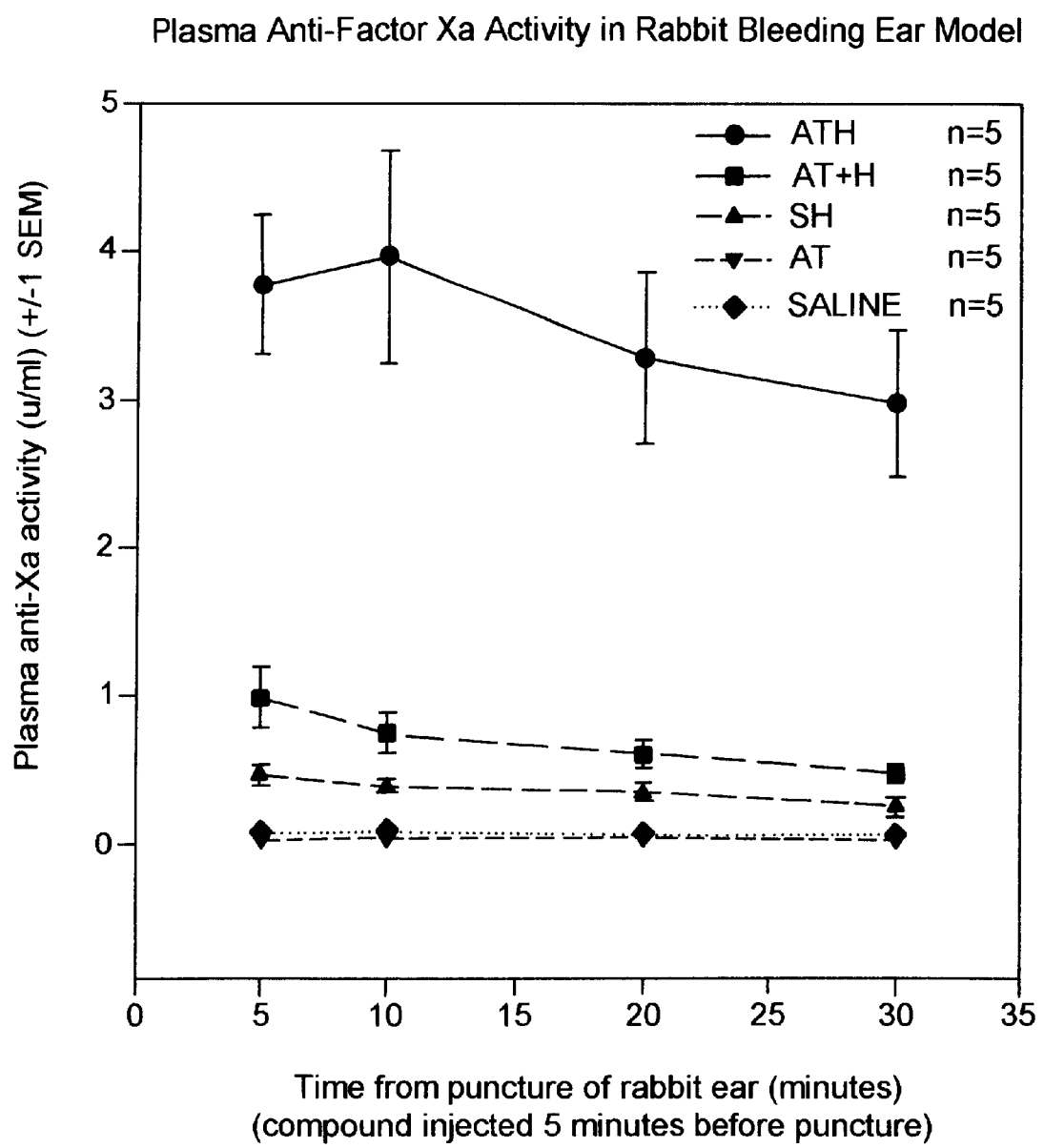
FIG. 18 shows plasma anti-factor Xa activity in a rabbit bleeding ear model.

FIG. 16 shows the cumulative blood loss over time. Bleeding was highest in the ATH group. One animal in the ATH group had significantly more bleeding than the rest of the animals in the same group. FIG. 17 shows the cumulative blood loss over time when this outlier was taken out of the analysis. The bleeding from the animals in the ATH group was well below the accepted amount of 200 pi blood loss over 30 minutes. Moreover, the cumulative blood loss in the first five minutes was essentially the same for all treatment groups that had anticoagulant. The increased cumulative blood loss in the ATH group is then likely due to its prolonged anti-factor Xa activity. The increased bleeding from ATH may also reflect the fact that anti-factor Xa activities were four times greater than those in the group that received AT+SH. FIG. 18 shows the plasma anti-factor Xa activity over time and demonstrates that anti-factor Xa activities of ATH last longer compared to the group that received AT+SH.

2. Comparison of ATH with Heparin in a Rabbit Venous Thrombosis Model

We evaluated ATH in a rabbit venous thrombosis treatment model. In these experiments ATH was compared to AT+SH, SH alone, AT alone and saline. The doses used were the same as those used for the rabbit bleeding ear model. The number of rabbits used for each group were n=5 for ATH, n=7 for AT+SH, n=8 for SH, n=5 for AT and n=5 for saline.

The rabbits were anaesthetized. The jugular vein was isolated and the side branches over 2 cm of the jugular vein ligated. The jugular vein segment was isolated with 2 tourniquets and a fogartry catheter inserted into the segment of vein. The endothelium was denuded by 15 passes of the inflated catheter and then 500 u of thrombin was injected into the segment. Then 0.2 ml of the rabbit's blood was injected into the segment to create a thrombus. At the same time 0.2 ml of the blood was placed into each of the two test tubes, acting as a control for the weight of the clot. Thirty minutes after the blood was injected into the vein, the tourniquets were released and the blood clot was exposed to systemic circulation. Ten minutes prior to the release of the tourniquets, the compounds tested were injected into the animals followed immediately by an injection of 125 I-human fibrinogen. A 2 ml citrated blood sample and 1 ml clotted blood sample were taken at 10, 20, 30, 60, 120 and 180 minutes after the tourniquets were released. The citrated blood samples were centrifuged to obtain platelet poor plasma and then stored at −70° C. These samples were subsequently assayed for anti-factor Xa activity. At 180 minutes, the animals were euthanised and thrombi recovered. The weight and radioactivity of the thrombi were compared with the control thrombi from the same animal.

Figure 19:
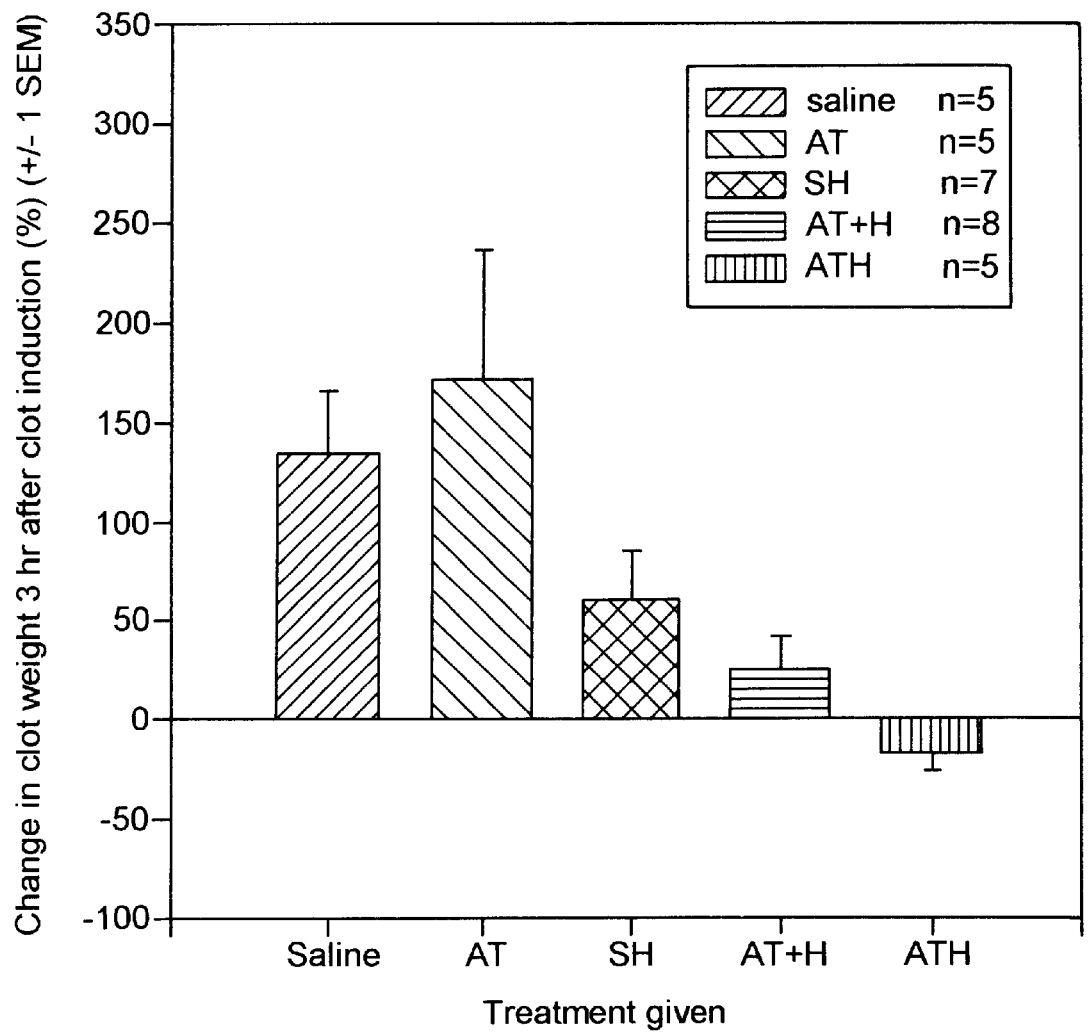
FIG. 19 shows the change in clot weight for different treatment groups in a rabbit venous thrombosis model.
Figure 20:
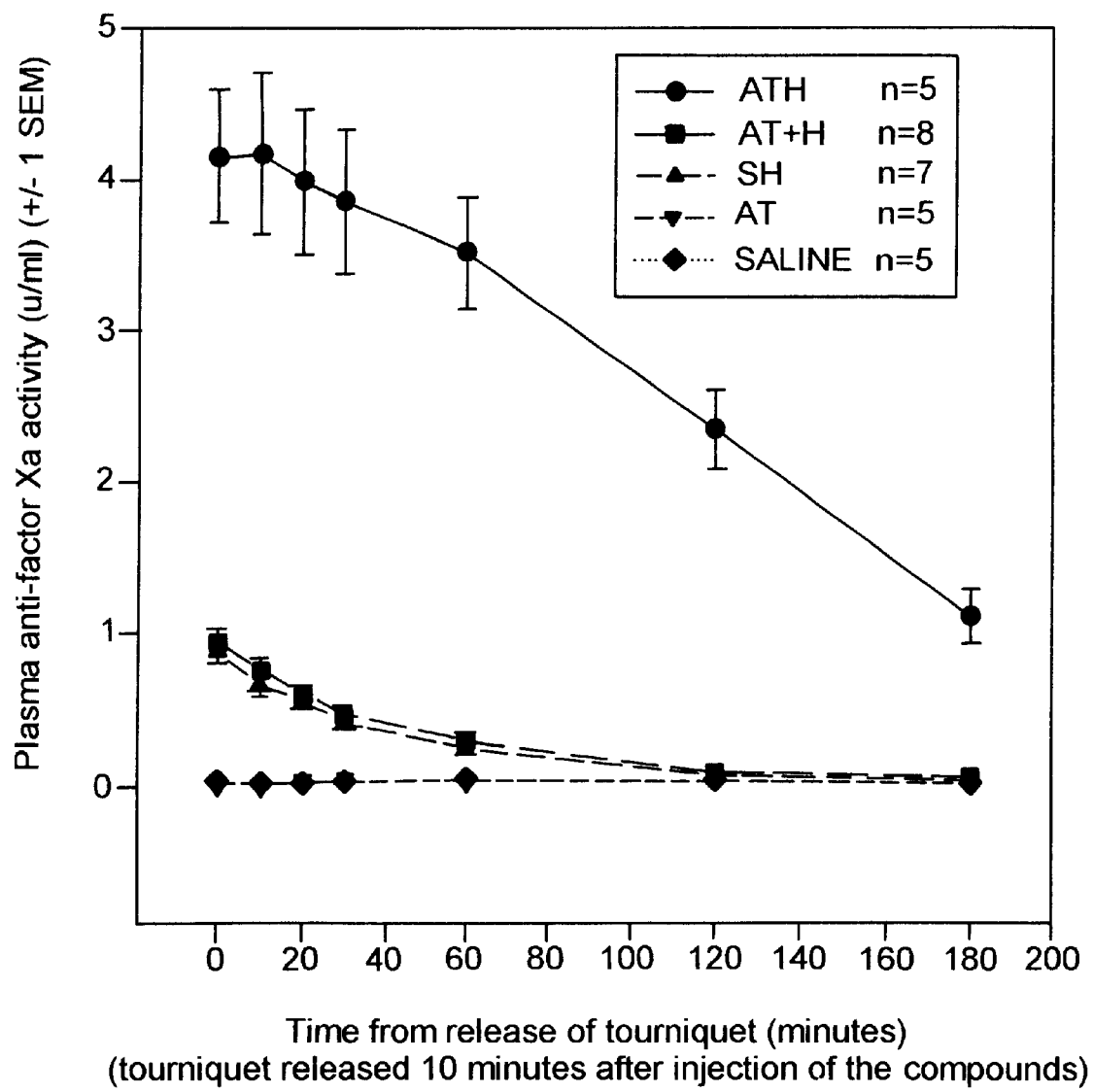
FIG. 20 shows plasma anti-factor Xa activity in a rabbit venous thrombosis model.

The model is designed to test the ability of an anticoagulant to prevent thrombus growth. The results shown in FIG. 19 indicate that ATH, AT+SH and SH were more effective than the saline control and AT control in preventing thrombus growth. However, ATH was the most effective treatment and was associated with an 18% reduction in thrombus size. The decrease in clot size was similar to results when agents that have activity towards fibrin bound thrombin were used. These data suggest that ATH has activity against fibrin bound thrombin. However, FIG. 20 shows that rabbits which received ATH had a higher anti-factor Xa activity compared to other groups. Therefore, it remains to be tested whether the more efficacious effect of ATH is due to a higher anti-factor Xa activity or to an accelerated activity of ATH itself.

It is likely that equivalent anti-factor Xa activities of heparin and ATH will result in less bleeding with ATH and that the reduced bleeding with ATH may be due to limited antiplatelet activity.

EXAMPLE VIII

ATH as a Local Anticoagulant to Coat a Prosthetic Surface

ATH was used as a local anticoagulant to coat thrombogenic prosthetic surfaces. To do this, a polyurethane-polycarbonate endovascular tubing from Corvita was coated with ATH by covalent linkage of the urethane groups to ATH by an intermediate monomer linker. The thrombogenecity of the coated tubing was tested in a Rabbit Jugular Vein Model (rabbit perfusion model), and compared to hirudin coated tubing, AT coated tubing and non-treated tubing.

1. Methods of Coating Polyurethane-polycarbonate with ATH Three steps are involved in the chemistry for coating ATH onto polyurethane-polycarbonate. First, the polymer of polyurethane-polycarbonate is activated with NaOCl. NaOCl reacts with urethane to make this relatively inert material chemically reactive. Second, a linking monomer (allyl glycidyl ether) is grafted onto the surface by reacting the activated tubing with an indicator ($Na_2S_2O_4$) and a monomer that can further react with other compounds such as ATH. Third, ATH (or other anticoagulants that have groups, such as, an amino group, that can react with the functional group of the monomer) is linked to the monomer.

2. Comparison of ATH Coated Tubing with Hirudin Coated Tubing

Hirudin was linked to polyurethane-polycarbonate tubing using the same method as that used for linkage of ATH. In these experiments, New Zealand White male rabbits were anaesthetized. The femoral artery and vein were cannulated with a cannula used for fluid administration and blood collection. The external jugular vein was exposed and a small segment of the facial vein partially occluded. A modified 14 gauge Angiocath (5 cm long) was inserted into the jugular vein. A 2 cm segment of the endovascular tubing was weighed and inserted into a modified 14 gauge Angiocath (5 cm long) catheter. The modification of the Angiocath consisted of cutting the tip off its stylet. The catheter was inserted 5 cm into the jugular vein via the partially occluded facial vein and the tubing then deployed. Thereafter, the catheter was withdrawn and the facial vein segment ligated. The tubing location can be seen through the jugular vein wall. Prior to insertion of the tubing and at 60, 120, 180 minutes after its deployment, 1 ml of blood was collected into citrate-PPACK as well as into citrate-THAT-M for thrombin-antithrombin complex (TAT) and fibrinopeptide A (FPA) analysis. At the end of 180 minutes, the segment of the external jugular vein containing the tubing was removed, flushed with 10 ml of saline and the outside diameter measured using callipers. Thereafter the segment of vein containing the tubing was opened longitudinally with scissors and the vein peeled off from the tubing. The tubing was cut longitudinally into two halves, blotted slightly on gauze and weighed. Blood samples were centrifuged immediately at 1,700 g, platelet-poor plasma obtained and frozen at −70° C. until assays were performed. The tubing were stored in 10% formalin for histopathology.

Figure 21:
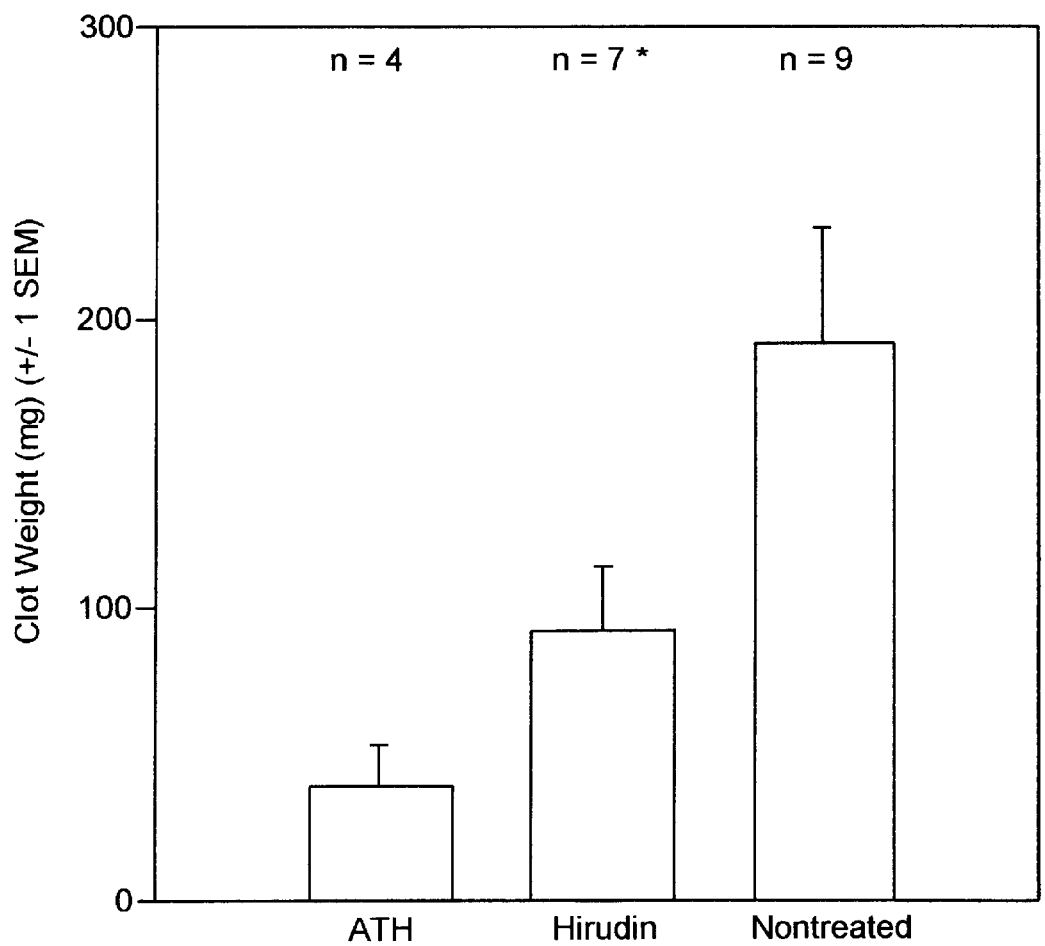
FIG. 21 shows the clot weights when ATH-grafted, hirudin-grafted, and untreated polyurethane tubing are used in a rabbit perfusion model.
Figure 22:
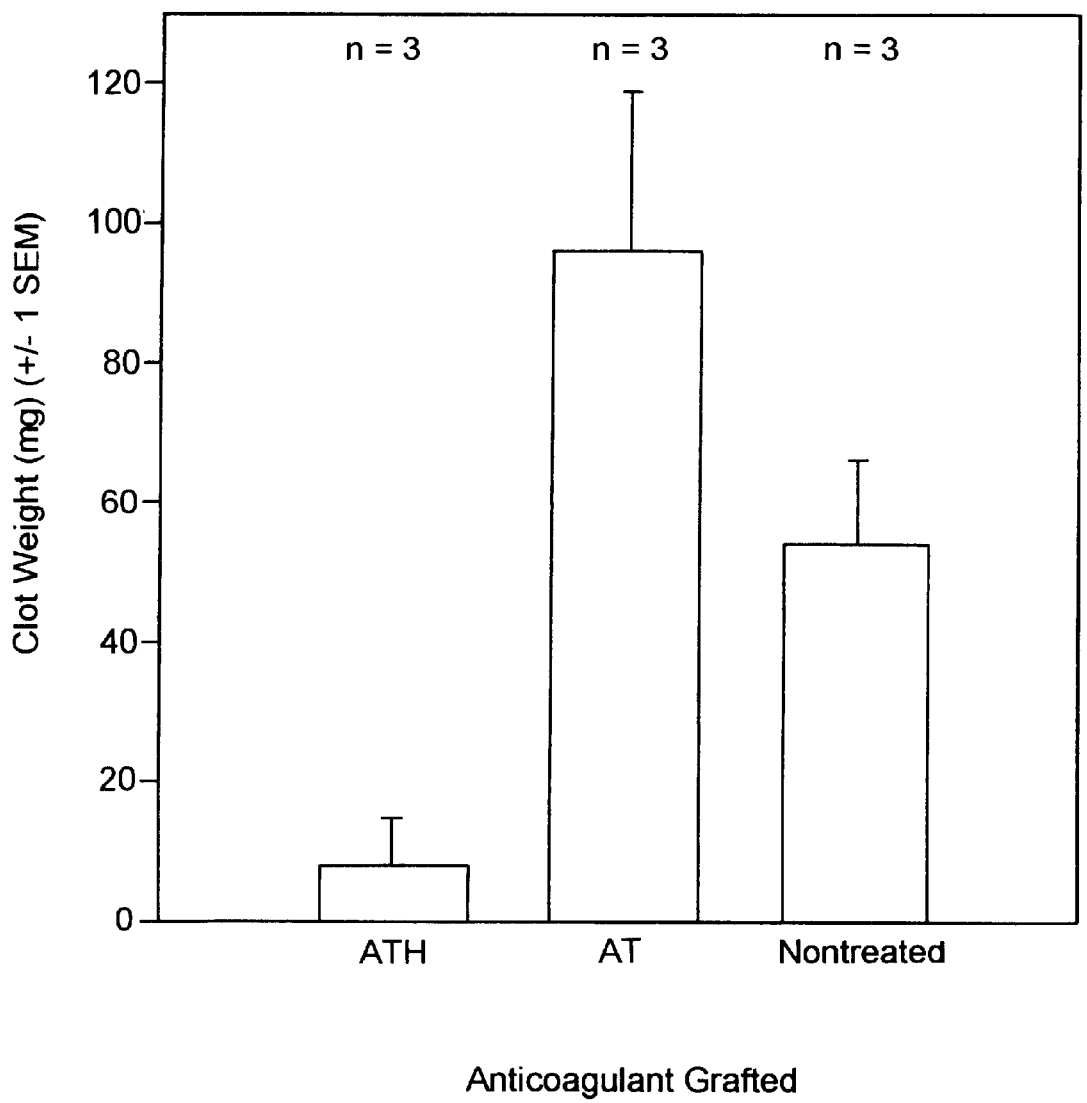
FIG. 22 shows shows the clot weights when ATH-grafted, AT-grafted, and untreated polyurethane tubing are used in a rabbit perfusion model.

FIG. 21 shows the weight of clots formed inside the tubing after they were inserted into rabbits for three hours. As shown in the graph, the weight of clots formed within the ATH coated tubing was statistically and strikingly less than that in the hirudin coated tubing, demonstrating that ATH coated tubing is more effective than Hirudin coated tubing 3. Comparison of ATH Coated Tubing with AT Coated Tubing and Non-treated Tubing The experimental procedures were the same as above. FIG. 22 shows the weight of clots that were formed inside tubing after the insertion into rabbits for three hours. ATH coated tubing induced smaller clots than AT coated tubing and non-treated tubing. Thus, the AT coated tubing was significantly more thrombogenic than ATH coated tubing.

Figure 23:
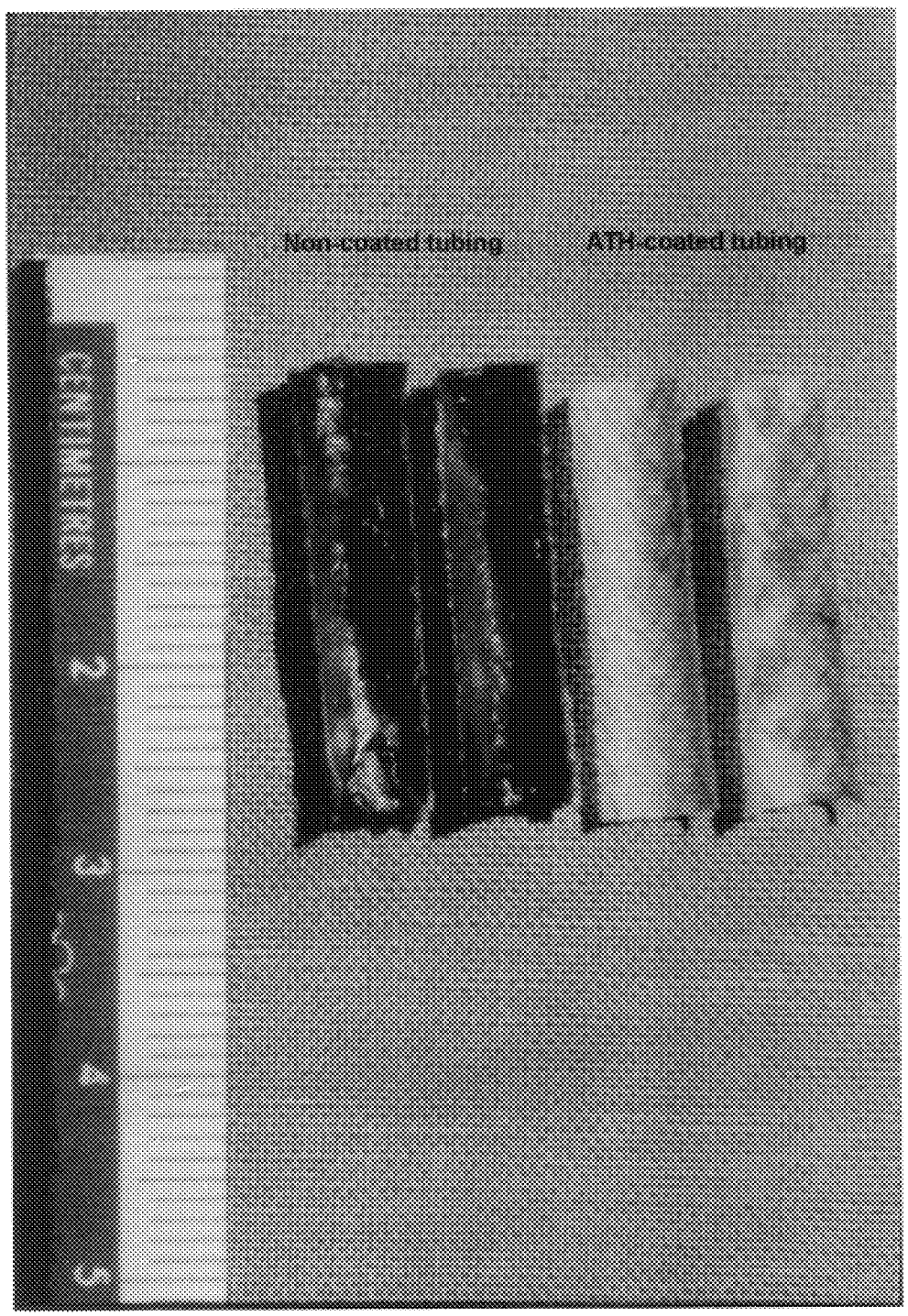
FIG. 23 shows the luminal surface of ATH-treated and untreated tubing after exposure to blood for three hours in rabbits.

FIG. 23 shows the luminal surface of an ATH coated tubing and a non-treated tubing after exposed to blood in a rabbit for three hours. The ATH coated tubing had minimal amount of blood clot on the surface but the non-treated tubing had clearly induced more clot.

EXAMPLE IX

Formation of ATH In Vivo Following Heparin Injection

To study in vivo ATH generation, rabbits were injected with heparin (200 U/kg intravenously and 400 U/kg subcutaneously followed after 3 h by 100 U/kg intravenously and 400 U/kg subcutaneously) and then, at 5 h after initial injection, exsanguinated into Na citrate (0.38% final concentration). Saturated $(NH_4)_2SO_4$ was added to the resultant plasma (1 μL/mL of plasma) to prevent any further Schiff base formation ex vivo. Covalent ATH generated in vivo was purified from plasma by initially collecting the supernatant after adding saturated $(NH_4)_2SO_4$ until 40% saturation was reached. After dialysis vs 0.01M Tris HCl pH 8.0, chromatography was carried out on DEAE Sepharose as described above. This was followed by chromatography on butyl agarose using the same method as the one described earlier except that elution of bound ATH was with 1.2M $(NH_4)_2SO_4$ in buffer. After concentration by pressure-dialysis, materials were analyzed by western immunoblotting using either an anti rabbit AT or anti human AT antibody raised in sheep (Affinity Biologicals).

Figure 27:
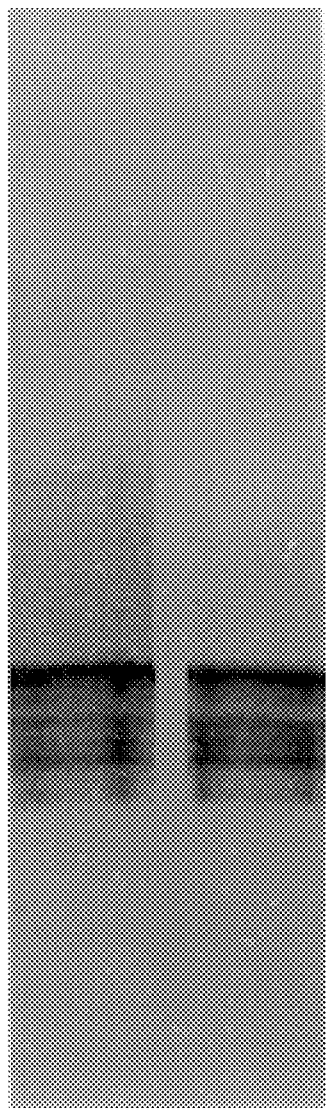
FIG. 27 shows a Western immunoblot of material isolated from plasma of rabbits injected with heparin. An antithrombin containing polydisperse, high molecular weight complex is present (lane 1) which disappears on treatment with heparinase, leaving only the antithrombin band.

FIG. 27 shows the results for a Western blot, developed using anti-rabbit AT antibody, of material recovered from the plasma of heparinized rabbits using a method adapted from the procedure for purification of covalent ATH produced in vitro. Polydisperse material, higher in molecular weight than rabbit AT, was recognized by the antibody (FIG. 27) which disappeared on treatment with heparinase (FIG. 27, lane 2). These data confirmed the presence of a species of ATH, produced in vivo, with the characteristics of a covalent complex. Western blots of AT, H and non covalent mixtures of AT+H showed no high molecular weight band, whereas an identical band compared to the in vivo material was observed with covalent ATH produced in vitro (data not shown).

In rabbits, 0.005% (by mass) of the peak level of H in plasma was recovered as ATH. Thus, injection of 7.5 mg of H subcutaneously in a rabbit yielded, after 4 h, 0.25 μg to 0.4 μg of ATH in terms of H.

Figure 28:
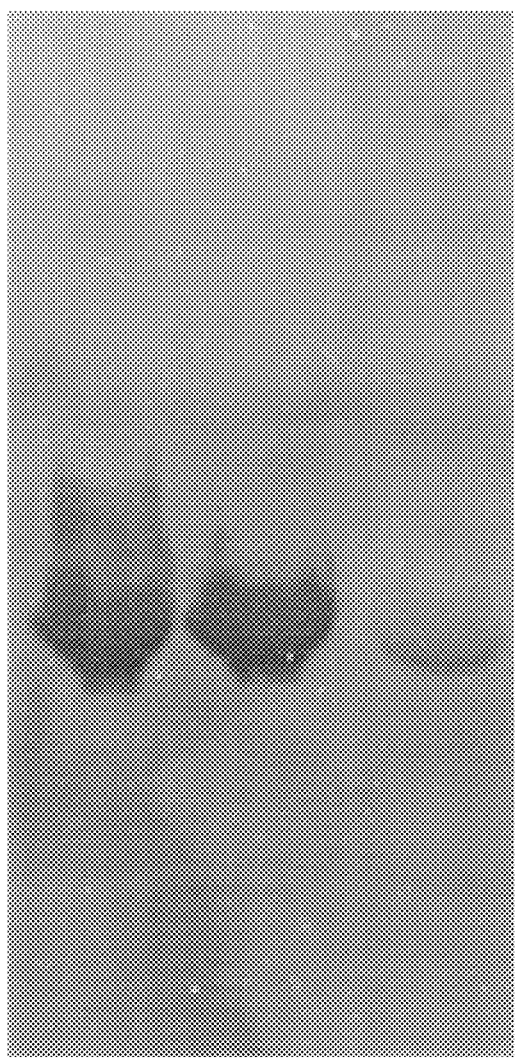
FIG. 28 shows a Western immunoblot of material isolated from plasma of a human injected with heparin. A high molecular weight antithrombin complex is seen (lane 1) which diminishes with heparinase treatment (lane 2), and is absent in the normal human plasma pool (lane 3). In both heparinase-treated and normal human plasma pool samples (lane 2 and lane 3, respectively), a band which corresponds to antithrombin without attached heparin is visible.

A single, subcutaneous injection of H to a human gave results similar to rabbits. 200U heparin/kg was injected subcutaneously into a female human followed, after 5 h, by removal of 100 mL of blood into citrate. The resultant plasma was then processed as described above for rabbits. A polydisperse, high molecular weight ATH complex was obtained which was not present in plasma from untreated humans (FIG. 28). Gels of the complex stained positively for H in the same region as the protein band. Laser densitometry of the blots was used to determine the amount of ATH generated (compared to a standard curve of ATH produced in vitro) from the H injected. The recovery of ATH in the plasma of the human subject was comparable to the results, described above, for rabbits.

These findings are the first demonstration of spontaneous formation of covalent polypeptide-polysaccharide complexes in an organism.

All patents, patent applications and publications described herein are incorporated by reference whether specifically incorporated previously or not.

Although the foregoing invention has been described in some detail by way of illustration and example for the purposes of clarity and understanding, it will be obvious that certain changes and modifications may be practiced within the scope of the appended claims.

What is claimed is:

1. A material for use in a medical or prosthetic device, said material comprising a polymer covalently attached to a covalent comjugate composition, said covalent conjugate composition comprising glycosaminoglycans linked to a species by covalent linkage, wherein the species comprises at least one primary amino group, and wherein the species is directly covalently linked via said amino group to a terminal aldose residue of the glycosaminoglycans, said covalent linkages comprising an α-carbonyl amine formed by a substantial amount of subsequent Amadori rearrangement of an imine resulting from reaction between said amino group and said terminal aldose residue of said glycosaminoglycans, wherein said glycosaminoglycans are heparin (H) and said amino-containing species is antithrombin III (AT).

2. A prosthetic or medical device comprising the material of claim 1.

3. The material of claim 1, wherein the polymer is a synthetic polymer selected from the group consisting of poly 2-hydroxyethyl methacrylate, poly acrylamide, polyether polyurethane urea (PEUU), polyethylene, polypropylene, polytetrafluoroethylene, poly(vinylchloride), polydimethylsiloxane, an ehtylene-acrylic acid copolymer, Dacron, polyester polyurethane, polyurethane, polycarbonate-polyurethane, polyamide (Nylon) and polystyrene.

4. The device of claim 2 selected from the group consisting of endovascular tubing, a central venous line, a cardiac catheter, a cardiopulmonary bypass circuit, a dialysis circuit, and an in vivo prosthesis.

5. The device of claim 4, wherein the device is endovascular tubing.

6. The device of claim 5, wherein the polymer is polyurethane-polycarbonate.

7. The device of claim 4, wherein the polymer is selected from the group consisting of poly 2-hydroxyethyl methacrylate, poly acrylamide, poly ether polyurethane urea (PEUU), polyethylene, polypropylene, polytetrafluoroethylene, poly(vinylchloride), polydimethylsiloxane, an ethylene-acrylic acid copolymer, Dacron, and polyester-polyurethane, polyurethane, polycarbonate-polyurethane, polyamide (Nylon) and polystyrene.

8. The device of claim 7, wherein the polymer is polycarbonate-polyurethane.

9. A material for use in a medical or prosthetic device, said material comprising a polymer in contact with a covalent conjugate composition, said covalent conjugate composition comprising glycosaminoglycans linked to a species by covalent linkages, wherein the species comprises at least one primary amino group, wherein the glycosaminoglycans are heparins, the species is antithrombin III, and the covalent conjugate composition comprises antithrombin III-heparin (ATH), said ATH being covalently attached to the polymer, and wherein the species is directly covalently linked via said amino group to a terminal aldose residue of the glycosaminoglycans to a substantial degree by an α-carbonyl linkage.

10. The material of claim 9, wherein the polymer is a synthetic polymer selected from the group consisting of poly 2-hydroxyethyl methacrylate, poly acrylamide, poly ether polyurethane urea (PEUU), polyethylene, polypropylene, polytetrafluoroethylene, poly(vinylchloride), polydimethylsiloxane, an ethylene-acrylic acid copolymer, Dacron, polyester-polyurethane, polyurethane, polycarbonate-polyurethane, polyamide (Nylon) and polystyrene.

11. A material for use in a medical or prosthetic device, said material comprising a polymer covalently attached to a covalent conjugate composition comprising a substantial amount of glycosaminoglycans covalently bonded to an amino-group containing species by, CO—$CH_2$—NH, said CO $CH_2$— portion being derived from said glycosaminoglycans and said —NH— portion from an amino group of said species, wherein said glycosaminoglycans are heparin (H) and said amino-containing species is antithrombin III (AT).

12. A material for use in a medical or prosthetic device, said material comprising a polymer covalently attached to a covalent conjugate composition comprising a substantial amount of a complex of the formula:

glycosaminoglycan CO—$CH_2$—NH-protein, wherein said glycosaminoglycan is heparin (H) and said protein is antithrombin III (AT).

13. A material of claim 1, wherein in said conjugate the molar ratio of amino-containing species to glycosaminoglycan is less than one.

14. A material of claim 11, wherein in said conjugate the molar ratio of amino-containing species to glycosaminoglycan is less than one.

15. A material of claim 12, wherein in said conjugate the molar ratio of protein to glycosaminoglycan is less than one.

16. A material for use in a medical or prosthetic device, said material comprising a polymer covalently attached to a covalent conjugate, said covalent conjugate comprising a glycosaminoglycan linked to a species by a covalent linkage, wherein the species comprises at least one primary amino group, and wherein the species is directly convalently linked via said amino group to a terminal aldose residue of the glycosaminoglycan, said covalent linkage comprising an α-carbonyl amine formed by (a) substantial subsequent Amadori rearrangement of an imine resulting from reaction between said amino group and said terminal aldose residue of said glycosaminoglycan and (b) isolation of the rearrangement product, wherein said glycosaminoglycan are heparin (H) and said amino-containing species is antithrombin III (AT).

17. A material of claim 1 wherein said linkages comprise an α-carbonyl amine formed by subsequent Amadori rearrangement to an extent of at least 80%.

18. A material of claim 1 wherein said linkages comprise an α-carbonyl amine formed by essentially complete subsequent Amadori rearrangement.

19. A material of claim 16 wherein said imine has undergone a subsequent Amadori rearrangement to an extent of at least 80%.

20. A material of claim 19 wherein said imine has undergone essentially complete subsequent Amadori rearrangement.

21. material of claim 9 wherein said substantial degree is to an extent of at least 80%.

22. A material of claim 21 wherein said substantial degree is an essentially complete degree.

23. a material of claim 11 wherein said substantial degree is to an extent of at least 80%.

24. A material of claim 12 wherein said substantial degree is to an extent of at least 80%.

25. A material of claim 11 wherein said substantial degree is an essentially complete degree.

26. A material of claim 12 wherein said substantial degree is an essentially complete degree.

27. A material of claim 1 pharmaceutically suitable for contacting blood in a human.

28. A material of claim 9 pharmaceutically suitable for contacting blood in a human.

29. A material of claim 11 pharmaceutically suitable for contacting blood in a human.

30. A material of claim 12 pharmaceutically suitable for contacting blood in a human.

31. A material of claim 16 pharmaceutically suitable for contacting blood in a human.

32. A material of claim 1 wherein said covalent conjugate composition is enriched in heparin chains having two pentasaccharides.

33. A material of claim 9 wherein said covalent conjugate composition is enriched in heparin chains having two pentasaccharides.

34. A material of claim 11 wherein said covalent conjugate composition is enriched in heparin chains having two pentasaccharides.

35. A material of claim 17 wherein said covalent conjugate composition is enriched in heparin chains having two pentasaccharides.

36. A material of claim 1 wherein said covalent conjugate composition comprises more than 10% heparin chains having two pentasaccharides.

37. A material of claim 9 wherein said covalent conjugate composition comprises more than 10% heparin chains having two pentasaccharides.

38. A material of claim 11 wherein said covalent conjugate composition comprises more than 10% heparin chains having two pentasaccharides.

39. material of claim 21 wherein said covalent conjugate composition comprises more than 10% heparin chains having two pentasaccharides.

40. A material of claim 1 wherein said covalent conjugate composition comprises more than 20% heparin chains having two pentasaccharides.

41. A material of claim 9 wherein said covalent conjugate composition comprises more than 20% heparin chains having two pentasaccharides.

42. A material of claim 11 wherein said covalent conjugate composition comprises more than 20% heparin chains having two pentasaccharides.

43. A material of claim 21 wherein said covalent conjugate composition comprises more than 20% heparin chains having two pentasaccharides.

44. A material for use in a medical or prosthetic device, said material comprising a polymer covalently attached to a covalent conjugate composition comprising glycosyaminoglycans and molecules comprising at least one amino group, wherein said amino group is directly linked to said glycosaminoglycans by covalent linkages, wherein said conjugate composition is made by the process comprising:

(a) incubating said glycosaminoglycans with said molecules at a pH and for a time sufficient for imine formation between said amino group and a terminal aldose residue of said glycosaminoglycans, and at a time and temperature sufficient for said imines to undergo a substantial amount of subsequent Amadori rearrangement to an α-carbonyl amine forming said covalent linkages;

(b) isolating said conjugate composition, or a pharmaceutically acceptable salt of said covalent conjugate composition, wherein said glycosaminoglycans are heparin (II) and said amino-containing species is antithrombin III (AT).

45. A material of claim 44 wherein said incubating is carried out for about two weeks.

46. A material of claim 11, wherein said substantial degree is more than 90%.

47. A material of claim 12, wherein said substantial degree is more than 90%.

48. A material of claim 1, wherein said substantial amount is more than 90%.

49. A material of claim 9, wherein said substantial degree is more than 90%.

50. A material of claim 16, wherein said substantial rearrangement is more than 90%.

51. A material of claim 11, which is stable at 4° C. for at least 60 days.

52. A material of claim 11, which is stable at 4° C. for at least 90 days.

53. A material of claim 11, wherein the heparin component stoichiometrically activates antithrombin III in the covalent conjugate.

54. A material of claim 11, wherein said covalent conjugate composition comprises more than 35% heparin chains having two pentasaccharides.

55. A material of claim 11, wherein said covalent conjugate composition comprises more than 50% heparin chains having two pentasaccharides.

56. a material of claim 11, wherein said conjugate is neutralized with protamine or human platelet factor 4.

57. A material of claim 11, wherein exosite 2 of thrombin is not required for said conjugate to bind thrombin.

58. A material of claim 11, wherein said conjugate activates antithrombin III molecules to be active catalytically, said molecules not being conjugated to said conjugate.

59. A material for use in medical or prosthetic device, saod material comprising a polymer covalently attached to a covalent conjugate composition, said covalent conjugate composition comprising glycosaminoglycans linked to a species by covalent linkages, wherein the species comprises at least one primary amino group, and wherein the species is directly covalently linked via amino group to terminal aldose residue of the glycosaminoglycans, said covalent linkages comprising an α-carbonyl amine formed by a substantial amount of subsquent Arnadori rearragement of an imine resulting from reaction between said amino group and said terminal aldose residue of said glycosaminoglycans.

* * * * *